(12) United States Patent
Stephenson, Jr. et al.

(10) Patent No.: US 9,074,236 B2
(45) Date of Patent: Jul. 7, 2015

(54) APPARATUS AND METHODS FOR MICROBIAL IDENTIFICATION BY MASS SPECTROMETRY

(71) Applicant: Oxoid Limited, Hampshire (GB)

(72) Inventors: James L. Stephenson, Jr., Raleigh, NC (US); Oksana Gvozdyak, Bedford, MA (US); Roger Grist, Crowborough (GB); Clay Campbell, San Jose, CA (US); Ian D. Jardine, Los Gatos, CA (US); Iain C. Mylchreest, Gilroy, CA (US)

(73) Assignee: OXOID LIMITED, Basingstoke, Hampshire (GB)

( * ) Notice: Subject to any disclaimer, the term of this patent is extended or adjusted under 35 U.S.C. 154(b) by 0 days.

(21) Appl. No.: 13/874,213

(22) Filed: Apr. 30, 2013

(65) Prior Publication Data

US 2014/0051113 A1    Feb. 20, 2014

Related U.S. Application Data

(60) Provisional application No. 61/687,785, filed on May 1, 2012.

(51) Int. Cl.
*C12Q 1/04* (2006.01)
*C12M 1/34* (2006.01)
*G01N 33/68* (2006.01)

(52) U.S. Cl.
CPC .............. *C12Q 1/04* (2013.01); *G01N 33/6848* (2013.01); *G01N 33/6851* (2013.01)

(58) Field of Classification Search
USPC .................................................. 435/34, 288.6
IPC ..................................... C12Q 1/04; C12M 1/34
See application file for complete search history.

(56) References Cited

U.S. PATENT DOCUMENTS

| | | | |
|---|---|---|---|
| 8,160,819 B2 | 4/2012 | Fagerquist et al. | |
| 8,224,581 B1* | 7/2012 | Wick et al. | 702/19 |
| 2002/0020670 A1 | 2/2002 | Petro | |
| 2002/0155587 A1 | 10/2002 | Opalsky et al. | |
| 2003/0068825 A1 | 4/2003 | Washburn et al. | |
| 2003/0124539 A1 | 7/2003 | Warrington et al. | |

FOREIGN PATENT DOCUMENTS

| | | |
|---|---|---|
| WO | 03049831 | 6/2003 |
| WO | 2006089103 | 8/2006 |
| WO | 2009065580 | 5/2009 |
| WO | 2009134120 | 11/2009 |
| WO | 2011006911 | 1/2011 |
| WO | 2012058632 | 3/2012 |
| WO | 2012058559 | 5/2012 |

OTHER PUBLICATIONS

Anonymous. The Thermofinnigan LCQ Classic (2014); downloaded from http://www.colorado.edu/chemistry/chem5181/ThermoFinnigan%20LCQ.pdf on May 5, 2014.*

Tipton et al. Analysis of Intact Protein Isoforms by Mass Spectrometry; The Journal of Biological Chemistry, vol. 286, No. 29 (Jul. 22, 2011) pp. 25451-25458.*

Verberkmoes et al. Integrating "Top-Down" and "Bottom-Up" Mass Spectrometric Approaches for Proteomic Analysis of Shewanella Oneidensis; Journal of Proteome Research, vol. 1 (2002) pp. 239-252.*

Frohm M. et al: "Biochemical and Antibacterial Analysis of Human Wound and Blister Fluid"; European Journal of Biochemistry, Published by Springer-Verlag on Behalf of the Federation of European Biochemical Societies; vol. 237, No. 1, Apr. 1, 1996, pp. 86-92, xp000863693, ISSN: 0014-2956, DOI: 10.1111/J.1432-1033.1996.0086n.x.

International Search Report and Written Opinion for PCT/US2013/039094 dated Sep. 27, 2013.

Barghouthi, Sameer A.; "A Universal Method for the Identification of Bacteria Based on General PCR Primers"; Indian J. Microbiol (Oct.-Dec. 2011) 51(4), pp. 430-444, Feb. 26, 2009.

Bergeron, et al.; "Preventing Antibiotic Resistance through Rapid Genotypic Identification of Bacteria and of Their Antibiotic Resistance Genes in the Clinical Microbiology Laboratory"; Journal of Clinical Microbiology, pp. 2169-2172, Aug. 1998.

Carroll, et al.; "Principles of Diagnostic Medical Microbiology"; Jawetz, Melnick, & Adelberg's Medical Microbiology, 26th Edition, chapter 47, pp. 753-784; Copyright 2013.

Claydon, et al.; "The rapid identification of intact microorganisms using mass spectrometry"; Nature Biotechnology, vol. 14, Nov. 1996.

Duguid, et al.; "Rapid Microbiological Methods: Where Are They Now?"; Nov. 1, 2011.

Fung, et al.: "Rapid Methods and Automation in Microbiology: 25 Years of Trends and Predictions of the Future" (date unknown).

Wattiau, et al.; "Methodologies for *Salmonella enterica* Subsp. *enterica* Subtyping; Gold Standards and Alternatives"; Applied and Environmental Microbiology, vol. 77, No. 22, Nov. 2011, pp. 7877-7885.

International Search Report for PCT/US2011/058452 dated Mar. 23, 2012.

International Search Report for PCT/US2006/005608 dated May 29, 2006.

(Continued)

*Primary Examiner* — Sharmila G. Landau
*Assistant Examiner* — Paul Martin
(74) *Attorney, Agent, or Firm* — Workman Nydegger

(57) ABSTRACT

Methods and systems for identification of microorganisms either after isolation from a culture or directly from a sample. The methods and systems are configured to identify microorganisms based on the characterization of proteins of the microorganisms via high-resolution/mass accuracy single-stage (MS) or multi-stage (MS") mass spectrometry. Included herein are also discussion of targeted detection and evaluation of virulence factors, antibiotic resistance markers, antibiotic susceptibility markers, typing, or other characteristics using a method applicable to substantially all microorganisms and high-resolution/mass accuracy single-stage (MS) or multi-stage (MS") mass spectrometry.

23 Claims, 24 Drawing Sheets

(56) References Cited

OTHER PUBLICATIONS

Van Der Vlis E et al. "Development of a needle device for on-line electroextraction-liquid chromatography," Journal of Chromatography A, Elsevier, Amsterdam, NL, vol. 741, No. 1, Aug. 9, 1996, pp. 13-21.

Bunger, et al, *Automated Proteomics of E. coli via Top-Down Electron-Transfer Dissociation Mass Spectrometry*, Mass Spectrometry Research Program, North Carolina, Analytical Chemistry, vol. 80, No. 5, Mar. 1, 2008, pp. 1459-1467.

Demirev, et al, *Mass spectrometry in biodefense*, Johns Hopkins University Applied Physics Laboratory, Laurel, MD, Journal of Mass Spectrometry Aug. 21, 2008, pp. 1441-1457.

Demirev, et al, *Top-Down Proteomics for Rapid Identification of Intact Microorganisms*, Johns Hopkins University Applied Physics Laboratory, Laurel, MD and Bruker Daltonics, Billerica, MA, Analytical Chemistry, vol. 77, No. 22, Nov. 15, 2005, pp. 7455-7461.

Fagerquist, et al, *Web-based Software for Rapid Top-Down Proteomic Identification of Protein Biomarkers, with Implications for Bacterial Identification*, Western Regional Research Center, Albany, CA and San Francisco School of Medicine, San Francisco, CA, Applied and Environmental Microbiology, vol. 75, No. 13, Jul. 2009, pp. 4341-4353.

Wynne, et al, *Phyloproteomic classification of unsequenced organisms by top-down identification of bacterial proteins using capLC-MS/MS on an Orbitrap*, Dept of Chemistry & Biochemistry, University of Maryland, College Park, MD and Department of Biochemistry and Molecular & Cellular Biology, Georgetown University Med. Ctr., Washington DC, Proteomics, vol. 10, 2010, pp. 3631-3643.

Wynne, et al, *Top-Down Identification of Protein Biomarkers in Bacteria with Unsequenced Genomes*, Dept of Chemistry & Biochemistry, University of Maryland, College Park, MD and Department of Biochemistry and Molecular & Cellular Biology, Georgetown University Med. Ctr., Washington DC, Analytical Chemistry, vol. 81, No. 23, Dec. 1, 2009, pp. 9633-9642.

\* cited by examiner

APPARATUS AND METHODS FOR MICROBIAL IDENTIFICATION BY MASS SPECTROMETRY

CROSS REFERENCE TO RELATED APPLICATIONS

This application claims the benefit of and priority to U.S. Prov. Pat. App. Ser. No. 61/687,785 entitled "Apparatus and methods for microbial analysis and directed empiric therapy" filed 1 May 2012 with inventors James Stephenson, Oksana Gvozdyak, Roger Grist, Clay Campbell and Ian Jardine, the entirety of which is incorporated herein by reference.

BACKGROUND

In recent years, mass spectrometry has gained popularity as a tool for identifying microorganisms due to its increased accuracy and shortened time-to-result when compared to traditional methods for identifying microorganisms. To date, the most common mass spectrometry method used for microbial identification is matrix-assisted laser desorption ionization time-of-flight (MALDI-TOF) mass spectrometry. In MALDI-TOF, cells of an unknown microorganism are mixed with a suitable ultraviolet light absorbing matrix solution and are allowed to dry on a sample plate. Alternatively, extract of microbial cells is used instead of the intact cells. After transfer to the ion source of a mass spectrometer, a laser beam is directed to the sample for desorption and ionization of the proteins and time-dependent mass spectral data is collected.

The mass spectrum of a microorganism produced by MALDI-TOF methods reveals a number of peaks from intact peptides, proteins, and protein fragments that constitute the microorganism's "fingerprint". This method relies on the pattern matching of the peaks profile in the mass spectrum of an unknown microorganism to a reference database comprising a collection of spectra for known microorganisms obtained using substantially the same experimental conditions. The better the match between the spectrum of the isolated microorganism and a spectrum in the reference database, the higher the confidence level in identification of the organism at the genus, species, or in some cases, subspecies level. Because the method relies upon matching the patterns of peaks in MALDI-TOF mass spectra, there is no requirement to identify or otherwise characterize the proteins represented in the spectrum of the unknown microorganism in order to identify it.

Although MALDI-TOF methods are rapid and cost effective, they have limitations that restrict the range of applications. The information content within a MALDI mass spectrum reflects the most abundant and ionizable proteins which, except for viral, are generally limited to ribosomal proteins at the experimental conditions used. Because ribosomal proteins are highly conserved among prokaryotes, differentiation of closely related microorganisms by MALDI-TOF is limited. Moreover, determination of strain and/or serovar type, antibiotic resistance, antibiotic susceptibility, virulence or other important characteristics relies upon the detection of protein markers other than ribosomal proteins which further limits the application of MALDI-TOF for microbial analysis. Laboratories using MALDI-TOF for identification of microorganisms must use other methods to further characterize the identified microbes. In addition, the MALDI-TOF method's reliance upon matching spectral patterns requires a pure culture for high quality results and is not generally suitable for direct testing of samples containing different microorganisms.

Several other mass spectrometry methods for detection of microorganisms have been used. For example, mass spectrometry-based protein sequencing methods have been described wherein liquid chromatography is coupled to tandem mass spectrometry (LC-MS/MS) and sequence information is obtained from enzymatic digests of proteins derived from the microbial sample. This approach, termed "bottom-up" proteomics, is a widely practiced method for protein identification. The method can provide identification to the subspecies or strain level as chromatographic separation allows the detection of additional proteins other than just ribosomal proteins, including those useful for characterization of antibiotic resistance markers and virulence factors. The main drawback of the bottom-up approach is the extended time to result due to the need for protein digestion, long chromatographic separation and data processing time. Therefore, this method is not amenable to high throughput approaches.

BRIEF SUMMARY

The present invention includes a novel method and system for identification of microorganisms either after isolation from a culture or directly from a sample based on the characterization of proteins of the microorganisms via high-resolution/mass accuracy single-stage (MS) or multi-stage ($MS^n$) mass spectrometry. Included herein are also discussion of targeted detection and evaluation of virulence factors, antibiotic resistance markers, antibiotic susceptibility markers, or other characteristics using a methodology applicable to substantially all microorganisms and high-resolution/mass accuracy single-stage (MS) or multi-stage ($MS^n$) mass spectrometry. And while the following discussion focuses on the identification of microorganisms via the characterization of proteins, the methods and systems discussed herein are equally applicable to the identification of microorganisms via the characterization of one or more of small molecules, lipids, or carbohydrates, and the like.

The present invention, in one aspect, offers an alternative to traditional bottom-up proteomics methods, namely top-down analysis of intact proteins derived from microbial cells via a method which is applicable to substantially all microorganisms including Gram positive bacteria, Gram negative bacteria, mycobacteria, mycoplasma, yeasts, viruses, and filamentous (i.e., microscopic) fungi. The present invention provides identification of microorganisms at the genus, species, subspecies, strain pathovar, and serovar level even in samples containing mixtures of microorganisms and/or microorganisms analyzed directly from pure and/or mixed cultures and from direct samples (e.g., surface swabs, bodily fluids, etc.). In addition, the approach can be employed for targeted detection of virulence factors, antibiotic resistance and susceptibility markers or other characteristics. The method of the present invention is simple and quick because there is no need for chemical or enzymatic digestion of a sample and data processing is accomplished in real time.

An exemplary method involves a two-phase process. In the first phase, soluble proteins from microbes present in a sample are quickly extracted and analyzed with a mass spectrometer to identify the microbes based upon molecular weight value and fragmentation analysis determined for one or more of the extracted soluble proteins. This first phase is performed within a few minutes, for example, less than 10 minutes, less than 5 minutes or within about one minute or less. The second phase utilizes rapid chromatographic separation and mass spectral analysis (e.g., targeted MS and $MS^n$) to further characterize the microbes identified in the first step, for example, by determining virulence factors, antibiotic resistance markers, antibiotic susceptibility markers or other characteristics. This second phase is performed in within a few minutes, for example, less than 15 minutes, less than 10 minutes or within about five minutes or less. Both phases rely on the detection and identification of intact proteins derived from the microbes, without chemical, physical or enzymatic degradation of those proteins to their substituent peptides.

Another exemplary method for identifying and characterizing one or more microbes in a sample includes steps of (a) performing a first analytical method using mass spectrometry to detect and identify one or more (e.g., one, two, three, four, five, or more) proteins from each of the one or more microbes, (b) using the identity of the one or more proteins from each of the one or more microbes to further identify at least one of the microbes in the sample, (c) using information from step (b) to automatically select a second analytical method from a list of pre-defined analytical methods, the second method also using mass spectrometry, and (d) performing the second analytical method on the sample to determine if proteins indicative of antibiotic resistance markers, antibiotic susceptibility markers and/or virulence factors are present in the sample and, optionally, quantifying the antibiotic resistance markers, antibiotic susceptibility markers and/or virulence factors present in the sample.

Target microorganisms include, without limitation, Gram-positive bacteria, Gram-negative bacteria, mycobacteria, mycoplasma, viruses, yeasts and filamentous fungi. The characterization process may include the detection of virulence factors, resistance markers, antibiotic susceptibility and any other molecules produced by the organisms of interest including, without limitation, those that impact clinical outcome. The method is applicable to a variety of different sample types, including samples from pure or mixed culture derived from clinical samples including, without limitation, blood, urine, stool, sputum, wound and body site swabs, and to samples derived from other sources including industrial or environmental samples such as food, beverage, soil, water, air, and swabs of surfaces.

The method of the present invention comprises at least one or more of the following steps: microbial cell disruption, solubilization of proteins, sample clean-up (to desalt, remove insoluble components and debris, and/or concentrate), sample infusion or flow injection, fast partial liquid chromatographic separation, ionization of proteins in solution, high-resolution/mass accuracy multi-stage mass spectrometry in MS and MS/MS mode, and microbial identification via molecular weight analysis and/or protein sequence analysis.

The system and sample preparation kits of the present invention provide means for performing the method. As contemplated in one embodiment, a rapid extraction procedure is followed by on-line clean up and direct analysis. In another embodiment, rapid extraction is followed by fast partial liquid chromatographic separation of intact proteins. The proteins are then ionized, for example, via electrospray ionization. The intact proteins are analyzed via MS and MS$^n$ in order to identify the microorganism to the genus, species, strain, subspecies, pathovar or serovar level, as needed. The MS or MS$^n$ methods can employ direct sequencing or pattern matching approaches for pathogen identification. The identification process occurs in real-time during the acquisition period. It can occur post-acquisition as well. The system further provides for quantitative detection and identification of virulence factors, resistance markers, antibiotic susceptibility markers and/or any other relevant markers, for example, those associated with disease.

Because a common method, using a limited set of reagents, is performed, the method of the present invention is suitable for use within a completely automated system for sample preparation and mass spectrometry.

Ideally, the method of the present invention is automated from sample preparation through results reporting. Results may be automatically transferred to a hospital's electronic medical records system where they can be directly linked to patient treatment strategies, insurance, billing, or used in epidemiological reporting. Such an integrated system facilitates epidemiological tracking of an outbreak at the hospital, local, regional, and global levels. For high throughput laboratories, multiple systems can be interfaced to a central computer which integrates data from the different instruments prior to reporting. The system can import phenotypic susceptibility data where it can be combined with identification, virulence, antibiotic resistance and typing information generated by the invention.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present disclosure, a more particular description of the disclosure will be rendered by reference to specific embodiments thereof, which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which.

DETAILED DESCRIPTION

The present invention, in one embodiment, provides a method for rapid extraction and analysis of a soluble protein extract from cells of at least one microorganism, including Gram positive bacteria, Gram negative bacteria, yeasts, mycobacteria, mycoplasma, microscopic fungi, and viruses. Analysis of proteins is performed via mass spectrometry to identify the microorganisms present in the sample and then, optionally, a targeted mass spectrometric analysis may be conducted to characterize (qualitatively and quantitatively) proteins associated with antibiotic resistance and/or sensitivity markers, virulence factors, typing of strains, or other characteristics. In another embodiment, kits comprising two or more of: reagents, consumables, devices, calibrators, controls, and standards for performing the method are provided.

Figure 1A:
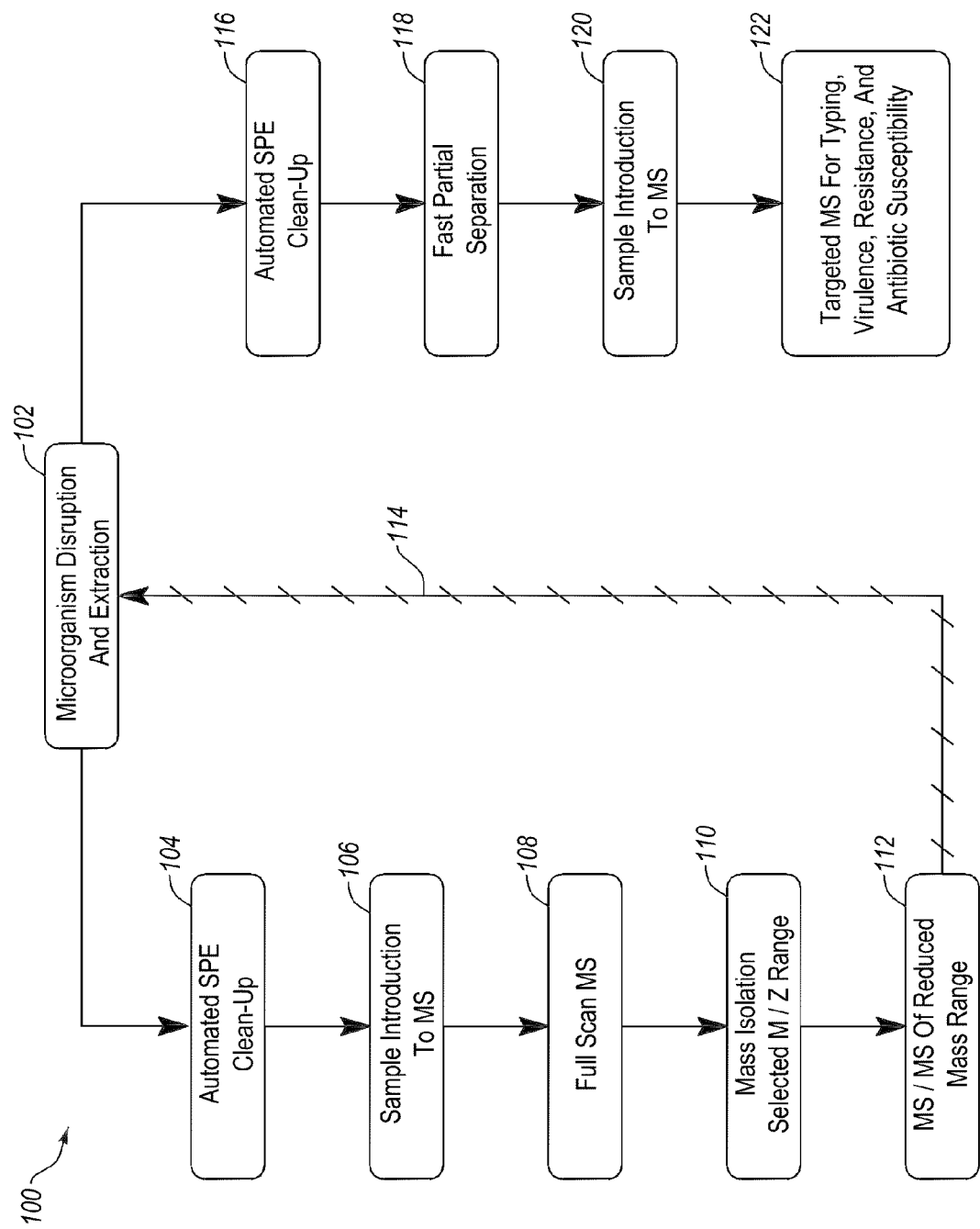
FIG. 1A is a flow diagram illustrating a method for identifying a microorganism.
Figure 2:
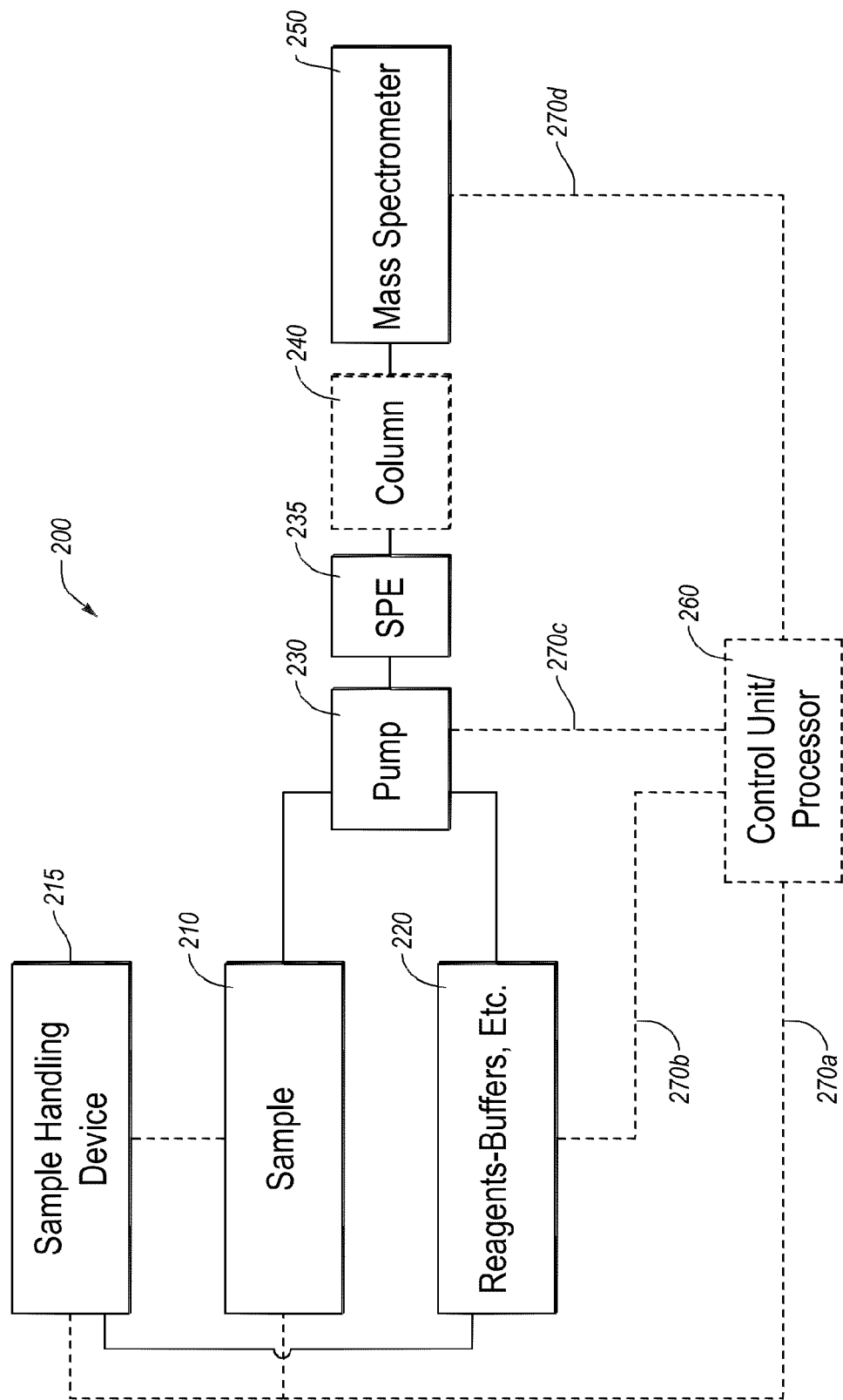
FIG. 2 is a block diagram schematically illustrating a system for rapid extraction and analysis of soluble proteins from at least one microorganism for identifying the at least one microorganism.

FIG. 1A provides an overview of the general work flow of the method 100 for rapid extraction and analysis of a soluble protein extract from cells of at least one microorganism. The steps of the method 100 may be performed manually using a variety of independent instruments and devices. Alternatively, some or all of the steps may be automated. An exemplary automated system suitable for performing the method 100 of FIG. 1A is illustrated in FIG. 2. Further discussion of the exemplary automated system may be found in WO 2012/058632 and WO 2012/058559, the entireties of which are incorporated herein by reference.

Referring now to FIG. 2, a system 200 for extraction of proteins from one or more microorganisms, detection of the proteins, and identification of the one or more microorganisms is schematically illustrated. The system 200 includes a sample handling device 215, a sample 210 that is accessible by the sample handling device 215, and reagents, buffers, and the like 220 that are fluidly coupled to the sample handling device 215. The system 200 further includes first and second solid phase extraction devices 235 (e.g., a solid phase extraction cartridge) configured for cleaning up (e.g., desalting, removing contaminants, concentrating proteins) and an optional chromatography column 240 that may be configured for at least partially purifying a sample 210 by liquid chromatography prior to mass-spec analysis. The sample 210, the first and second extraction devices 235, and the optional chromatography column 240 are in fluid communication with a fluid handling pump 230, the reagent 220, and a mass spectrometer 250.

The sample handling device 215 is capable of preparing a range of sample types containing one or more microbes and delivering a soluble protein fraction extracted from the microbes to the mass spectrometer 250 for analysis. A sample 210 may be of any type suspected to contain one or more microorganisms including, without limitation, isolated colonies from a culture plate, cells from liquid growth medium, blood, saliva, urine, stool, sputum, wound and body site swabs, soil, food, beverage, water, air, and environmental surface swabs.

The sample handling device 215 may include one or more of a cell disruption means, a robotic liquid handling means, a centrifuge, filtration means, an incubator, mixing means, a vacuum pump, a fluid pump, and reagents 220 that can be used for disruption of microbes and isolation of a soluble protein fraction. Disruption of bacterial, fungal, mycoplasma cells, viruses, and the like may be achieved by mechanical, chemical, enzymatic and other means as are commonly known in the art. Mechanical approaches include bead beating, use of pressure like French press and the like, sonication or other methods known in the art. Chemical methods include exposure to chaotropes such as urea, thiourea, or guanidine HCL to lyse the microbial cells and solubilize their contents. Alternatively, organic acid/solvents mixtures may be utilized to disrupt cells. Enzymatic methods include using lysozyme, lysostaphin or other lytic enzymes to form "holes" in the bacterial cell walls that allow the contents to leak out into the surrounding solution.

As illustrated in FIG. 2, the system 200 further includes an optional control unit 260 that can be linked to various components of the system 200 through linkages 270a-270d. For example, the control unit 260 can be linked to the sample 210 to control sample application, the reagents 220 to control the application of various reagents, the pump 230 to control fluid handling, flow rates, etc., to the sample handling device 215 to control sample preparation, and to the mass spectrometer 250 to control mass spectrometry parameters. In the illustrated embodiment, the control unit 260 can also serve as a data processing unit to, for example, process data from the mass spectrometer 250 or to forward the data to server(s) for processing and storage (the server is not shown in FIG. 2), The Control Unit 260 can also be used to automatically forward the results to health care professionals.

In some embodiments, the system 200 is designed to be used by a clinician or a general laboratory technician who is not necessarily expert in all aspects of sample preparation, LC-MS operations, LC-MS methods development, and the like. As such, the control unit 260 can be designed to encapsulate the data system environment by providing a user with a simplified application interface that can be used to initiate and monitor essentially all aspects of assaying a sample 210 without requiring the user to interact with the overall hardware and control systems of the system 200. The control unit 260 is therefore configured to provide a degree of separation between the user and the underlying services that control devices, data files and algorithms for translating data to a user readable form. That is, the control unit 260 eliminates the need for the user to be aware of or in control of hardware for analyzing clinical samples and provides a simplified interface to send and receive information from the mass spectrometer.

The control unit 260 may be configured to internally monitor each sample analysis request and is capable of tracking the analysis request from start to finish through the system 200. Once data for a sample 210 is being acquired or has been acquired by the system 200, the control unit 260 may be configured to automatically start post processing the data based on the type of assay selected by the user. Moreover, the control unit 260 can be configured to automatically select post processing parameters based on the type of assay selected by the user, further reducing the need for the user to interact with the system once the assay has been selected and started for analysis. The control unit 260 can be designed as a layer that fits between the system 200 and the user to reduce the complexity needed to set up sample assays for acquisition. The control system 260 can also be configured to return only the most relevant data to the user to avoid overwhelming the user with extraneous information.

In one embodiment, the system 200 can further include a sample detection device (not pictured) operably coupled to or integrated with the sample handling device 215. The sample detection device can work with the sample handling device 215 or independently of the sample handling device 215 perform at least one of the following functions:
  i. identify samples entering the system;
  ii. identify assay types for the samples entering the system;
  iii. select an assay protocol based on the anticipated assay type and/or analyte of interest;
  iv. direct the sample handling device and/or the control system to initiate analysis of the analyte of interest in the sample;
  v. direct the control system to select one or more reagents based upon the assay protocol selected for the type of assay and/or analyte of interest;
  vi. direct the control system to select a liquid chromatography mobile phase condition based upon the assay protocol selected for the type of assay and/or analyte of interest and cause the liquid chromatography system to perform the assay and/or purify the analyte of interest;
  vii. direct the control system to select a mass spectrometer setting based upon the assay protocol selected for the assay type and/or analyte of interest and cause the mass spectrometer to create mass spectral data associated with the selected assay type and/or analyte of interest; or
  viii. direct the control system to analyze the mass spectral data associated with the selected assay type and/or analyte of interest to identify the presence and/or concentration of the analyte of interest.

The sample, or the processed sample, may be cleaned up and or purified prior to analysis by mass spectrometry. Such purification, or sample clean-up, may refer to a procedure that removes salts or lipids from the crude cell extract, or to a procedure that enriches one or more analytes of interest relative to one or more other components of the sample. In one embodiment, such purification, or sample clean-up, may be accomplished by the protein extraction devices 235 and/or the optional chromatography column 240.

In one embodiment, the first and/or second extraction device 235 may include a solid phase extraction (SPE) cartridge. In some embodiments, the SPE cartridge 235 may be in line directly with the high resolution/high mass accuracy mass spectrometer 250. In one embodiment, the SPE cartridge may be a polypropylene tip with a small volume of silica or other sorbent containing bonded $C_4$, $C_8$ or $C_{18}$ or other functional groups immobilized in the cartridge, for example, a StageTip™ cartridge (Thermo Fisher Scientific). In alternative embodiments, polymeric sorbents or chelating agents may be used. The bed volume may be as small as 1 μL or less but greater volumes may also be used. The apparatus and method are well suited to the complex samples derived from the microbial cells because each SPE cartridge is used only once, minimizing carryover problems from one sample to another.

In one embodiment, the optional chromatography column 240 may include column configured for at least partial chromatographic separation of the proteins in the sample. The stationary phase in the chromatography column may be porous or non-porous silica or agarose particles, or a monolithic material polymerized or otherwise formed inside the column. The stationary phase may be coated with an appropriate material such as $C_{18}$, $C_8$, $C_4$ or another suitable derivative, or contain cation exchanger or other material, or the combination of the above to facilitate the separation of the proteins, and such material may be chemically bonded to the particles or monolith inside the column. Particle sizes typically range from about 1.5 to 30 μm. Pore sizes can range from 50 to 300 angstroms. Inside diameters of columns typically range from about 50 μm to 2.1 mm, and column length from about 0.5 cm to 25 cm, or other. The mobile phase or eluent may be a pure solvent, or a mixture of two or more solvents, and may contain added salts, acids and/or other chemical modifiers. The proteins are separated on the column based on one or more physiochemical properties, including size, net charge, hydrophobicity, affinity, or other physiochemical properties. Chromatographic separation methods include one or more of ion exchange, size exclusion, HILIC, hydrophobic interaction, affinity, normal-phase, or reverse-phase chromatography.

Additional methods of purifying the samples may include, without limitation, liquid chromatography, HPLC, UHPLC, precipitation, solid-phase extraction, liquid-liquid extraction, dialysis, affinity capture, electrophoresis, filtration, ultrafiltration or other suitable methods known in the art, are used for the purification.

Various methods have been described involving the use of HPLC for sample clean-up prior to mass spectrometry analysis. One of skill in the art can select HPLC instruments and columns that are suitable for use in the invention. The chromatographic column typically includes a medium (i.e., a packing material) to facilitate separation of chemical moieties in space and time. The medium may include minute particles. The particles may include a bonded surface that interacts with the various chemical moieties to facilitate separation of the analytes of interest. One suitable bonded surface is a hydrophobic bonded surface such as an alkyl bonded surface. Alkyl bonded surfaces may include $C_4$, $C_8$, or $C_{18}$ bonded alkyl groups, preferably $C_{18}$ bonded groups. The chromatographic column includes an inlet port for receiving a sample and an outlet port for discharging an effluent that includes the fractionated sample. For example, a test sample may be applied to the column at the inlet port, eluted with a solvent or solvent mixture, and discharged at the outlet port. In another example, more than one column may be used sequentially or as a 2D chromatography wherein a test sample may be applied to a first column at the inlet port, eluted with a solvent or solvent mixture onto a second column, and eluted with a solvent or solvent mixture from the second column to the outlet port. Different solvent modes may be selected for eluting the analytes. For example, liquid chromatography may be performed using a gradient mode, an isocratic mode, or a polytyptic (i.e. mixed) mode.

The terms "mass spectrometry" or "MS" as used herein refer to methods of filtering, trapping, detecting, and measuring ions based on their mass-to-charge ratio, or "m/z" (also sometime referred to as "Da/e"). In general, one or more molecules of interest, such as microbial proteins, are ionized and the ions are subsequently introduced into a mass spectrometric instrument where, due to a combination of electric or magnetic and electric fields, the ions follow a path in space that is dependent upon mass ("m" or "Da") and charge ("z" or "e").

The mass spectrometer 250 will include an ion source for ionizing the fractionated or not fractionated sample and creating charged molecules for further analysis. For example ionization of the sample may be performed by electrospray ionization (ESI). Other ionization techniques include, but are not limited to, atmospheric pressure chemical ionization (ACPI), photo-ionization, electron ionization (EI), chemical ionization (CI), fast atom bombardment (FAB)/liquid secondary ion mass spectrometry (LSIMS), matrix-assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., m/z) and signal intensity. Suitable analyzers for determining mass-to-charge ratios include quadrupole analyzers, ion trap analyzers, Fourier transform ion cyclotron resonance (FTICR) analyzers, electrostatic trap analyzers, magnetic sector analyzers and time-of-flight analyzers. The ions may be detected by using several detection modes. For example, selected ions may be detected (i.e., using a selective ion monitoring mode (SIM)), or alternatively, ions may be detected using selected reaction monitoring (SRM) or multiple reaction monitoring (MRM) (MRM and SRM are essentially the same experiment). Ions can also be detected by scanning the mass analyzers to detect all ions from the sample.

In one embodiment, the mass-to-charge ratio may be determined using a quadrupole analyzer. For example, in a "quadrupole" or "quadrupole ion trap" instrument, ions in an oscillating radio frequency (RF) field experience a force proportional to the amplitude of the RF signal, the direct current (DC) potential applied between electrodes, and the ion's m/z ratio. The voltage and amplitude can be selected so that only ions having a particular m/z travel the length of the quadrupole, while all other ions are deflected. Thus, quadrupole instruments can act as a "mass filter," a "mass separator" or an ion lens for the ions injected into the instrument.

One can often enhance the resolution of the MS technique by employing "tandem mass spectrometry" or "MS/MS" for example via use of a triple quadrupole mass spectrometer. In this technique, a first, or parent, or precursor, ion generated from a molecule of interest can be filtered in an MS instrument, and these precursor ions subsequently fragmented to yield one or more second, or product, or fragment, ions that are then analyzed in a second MS procedure. By careful selection of precursor ions, only ions from specific analytes are passed to the fragmentation chamber (e.g., a collision cell), where collision with atoms of an inert gas produce these product ions. Because both the precursor and product ions are produced in a reproducible fashion under a given set of ionization/fragmentation conditions, the MS/MS technique can provide an extremely powerful analytical tool. For example, the combination of ion selection or filtration and subsequent fragmentation can be used to eliminate interfering substances, and can be particularly useful in complex samples, such as biological samples.

In another embodiment, the mass-to-charge ratio may be determined using a hybrid mass spectrometer system containing an electrostatic ion trap mass analyzer capable of high resolution and accurate mass determination, for example a Q-Exactive™ mass spectrometer system (Thermo Fisher Scientific) which contains a quadrupole mass analyzer and an Orbitrap™ mass analyzer. Here, ions are selected by the quadrupole mass analyzer, then passed into a trapping device where the given ion population is collected, collisionally cooled, and injected at high energy and precise trajectory into the Orbitrap mass analyzer. Alternately, precursor ions are selected by the quadrupole mass analyzer, passed to a collision cell where product ions are produced, which are then passed into a trapping device where the given ion population is collected, collisionally cooled, and injected at high energy and precise trajectory into the Orbitrap mass analyzer. Ions oscillate axially across the trap at a frequency proportional to $(z/m)^{1/2}$ where z is the charge on the ion and m is the mass. The image current of these oscillating ions is detected and that frequency domain data is converted into mass spectral information using the principle of Fourier transforms. The longer the transient collection time, the high the resolution for the subsequent mass spectral data. High resolution data can be obtained at values in excess of 200,000 with mass accuracies of 5 ppm or better.

For example, a flow of liquid solvent from a chromatographic column, possibly containing one or more analytes of interest, enters the heated nebulizer interface of a LC-MS/MS analyzer and the solvent/analyte mixture is converted to vapor. Ions derived from the analytes of interest may be formed in the liquid phase and subsequently ejected into the gas phase by nebulization in the ESI source or by reactions between neutral analytes and reactive ions as the analytes enter the gas phase.

The ions pass through the orifice of the instrument and passes a range of lenses, quadrupole, hexapole and similar devices prior to entering the instrument. In one embodiment, selected m/z windows of any m/z value (e.g., a 3, 5, 10, 20, 30, 40, 50, 100, 1800 or more dalton range of m/z) may be analyzed to determine the molecular weights of the intact proteins in the window(s). In general, smaller m/z window sizes may improve signal-to-noise. In addition to the above stated m/z window sizes, the m/z window size may be adjusted dynamically anywhere depending on experimental conditions. In another embodiment, pre-determined ion(s) from the window(s) are allowed to pass into the collision cell where they collide with neutral gas molecules (e.g., argon, nitrogen, or the like) and fragment. The fragment ions generated are passed into the mass analyzer where the fragment ions are separated and forwarded to the detector. In other embodiments, other fragmentation processes may include, but are not limited to, the absorption of infrared photons via infrared multiple photon dissociation (IRMPD), the absorption of a single UV photon, through ion-ion reactions including electron transfer dissociation (ETD), or collisional-activation of electron transfer product ions which do not undergo prompt fragmentation, electron capture dissociation (ECD). In an exemplary embodiment, the dissociation method is the high energy collision-induced dissociation (HCD). As ions collide with the detector they produce analog signal which is further converted to a digital signal.

The acquired data is relayed to a computer, which plots voltage versus time. The resulting mass chromatograms are similar to chromatograms generated in traditional HPLC methods. Concentrations of the analytes of interest may be determined by calculating the area under the peaks in the chromatogram, if there are any chromatographic peaks, or using the intensity of peaks in mass spectrum. The concentration of the analyte or analytes of interest (e.g., proteins) in the sample is accomplished via one of many different techniques know in the state of the art involving external or internal calibrations, relative quantitation, peak height or area counts, standard addition, or any other method known in the state of the art.

A. Identification of Microorganism(s)

I. Microorganism Disruption and Solubilization of Proteins

Referring again to FIG. 1A, as shown in step a 102, a sample suspected of containing one or more microorganisms may be disrupted and treated to obtain microbial cells directly from the sample (for example, urine), or may be used to isolate pure cultures. Microbial cells are then used to produce a soluble fraction of proteins. The sample may be of any type suspected to contain one or more microorganisms including, without limitation, isolated colonies from a culture plate; cells from liquid growth medium; blood, saliva, urine, stool, sputum, wound and body site swabs; food and beverage; soil, water, air; environmental and industrial surface swabs.

Cell disruption may be achieved by mechanical, chemical, enzymatic means as are commonly known in the art and discussed in greater detail above with respect to FIG. 2. After disruption, the insoluble portion of the sample (typically cell wall material, certain lipids, precipitated proteins, and other cellular components) may be removed from the solution via centrifugation, filtration (either manual or automated) or other methods known in the art. Sample preparation may be automated using robotic systems controlled by one or more computers (see FIG. 2, 202 and 215). Such robotic systems may be part of a larger system and linked to other devices or computers.

In one example, a 1 mm bacteriological loop is used to collect cells of actively growing *E. coli* from the surface of a suitable culture plate, for example OXOID™ Tryptone Soya agar plate (Thermo Fisher Scientific). The cells are suspended in 70% ethanol in LC/MS grade water and, after treatment for several minutes, the sample is centrifuged and supernatant is discarded. The cells are then subjected to lysis using 2.5% trifluoroacetic acid in ACN:water (1:1), after which the sample is centrifuged for about 5 minutes at 14,000 rpm to remove insoluble components. Following centrifugation, the supernatant is transferred to a new tube and may be routinely fully evaporated either by using a speedvac, or under a flow of nitrogen. Prior to analysis, the sample is reconstituted either in 2% ACN, 98% water with 0.2% formic acid (when the use of chromatography is anticipated), or in ACN:water (1:1) with 2% formic acid for flow injection or direct infusion. The reconstituted sample is then subjected to direct analysis by high resolution mass spectrometry or undergoes fast partial chromatographic separation and analysis by high resolution mass spectrometry.

In another example, a 2 mm bacteriological loop may be used to collect approximately 10 mg (wet weight) of cells of actively growing culture (e.g., *Escherichia coli, Staphylococcus xylosus, Kocuria rosea, Bacillus liheniformis, Mycobacterium smegmatis* or other) from the surface of a suitable culture plate, for example OXOID™ Tryptone Soya agar plate (Thermo Fisher Scientific). The cells are transferred to a 0.5 ml microcentrifuge tube and 20 µl of solution of 50% formic acid in 25% acetonitrile, 25% water is added; the pipette volume is increased to 40 µl; and the suspension is vigorously pipetted up and down until the cells are disrupted, as indicated by the appearance of a foam. Then 180 µl of acetonitrile:water (1:1) is added and the resulting solution is centrifuged for approximately 5 minutes at 14,000 rpm. The supernatant is removed and diluted as needed for either direct infusion or flow injection.

In another example, centrifuge is used to collect cells of *Candida albicans* from the liquid growth medium, for example Sabouraud liquid medium (OXOID™, Thermo Fisher Scientific). The cells are washed from the growth medium with 0.9% physiological saline three times and sedimented. The cells may then be pre-treated with a mixture of ethanol and methyl tert-butyl ether (7:3) at room temperature for 10 min or less. The cells are sedimented by centrifugation and supernatant is discarded. A mixture that includes about 70% formic acid, 15% acetonitrile and 15% water may be used to lyse the cells and solubilize proteins. Insoluble components are sedimented at 14,000 rpm for 5 min, supernatant is transferred to a clean vial or centrifugal tube and is diluted with 0.2% formic acid in acetonitrile:water (2:98) prior to chromatography. When no chromatography is anticipated, the supernatant is diluted in a way to adjust concentrations of solvents to acetonitrile:water (1:1), 0.2-2% formic acid. Instead for acetonitrile, methanol can also be used. After centrifugation, the diluted supernatant is then subjected to in-line solid phase extraction with or without fast partial chromatographic separation and analysis by high resolution mass spectrometry. Alternatively, the sample in acetonitrile:water (1:1), 0.2-2% formic acid is either flow injected, or directly infused into a mass spectrometer for the analysis.

II. Sample Desalting, Concentration and Chromatographic Separation

Figure 3:
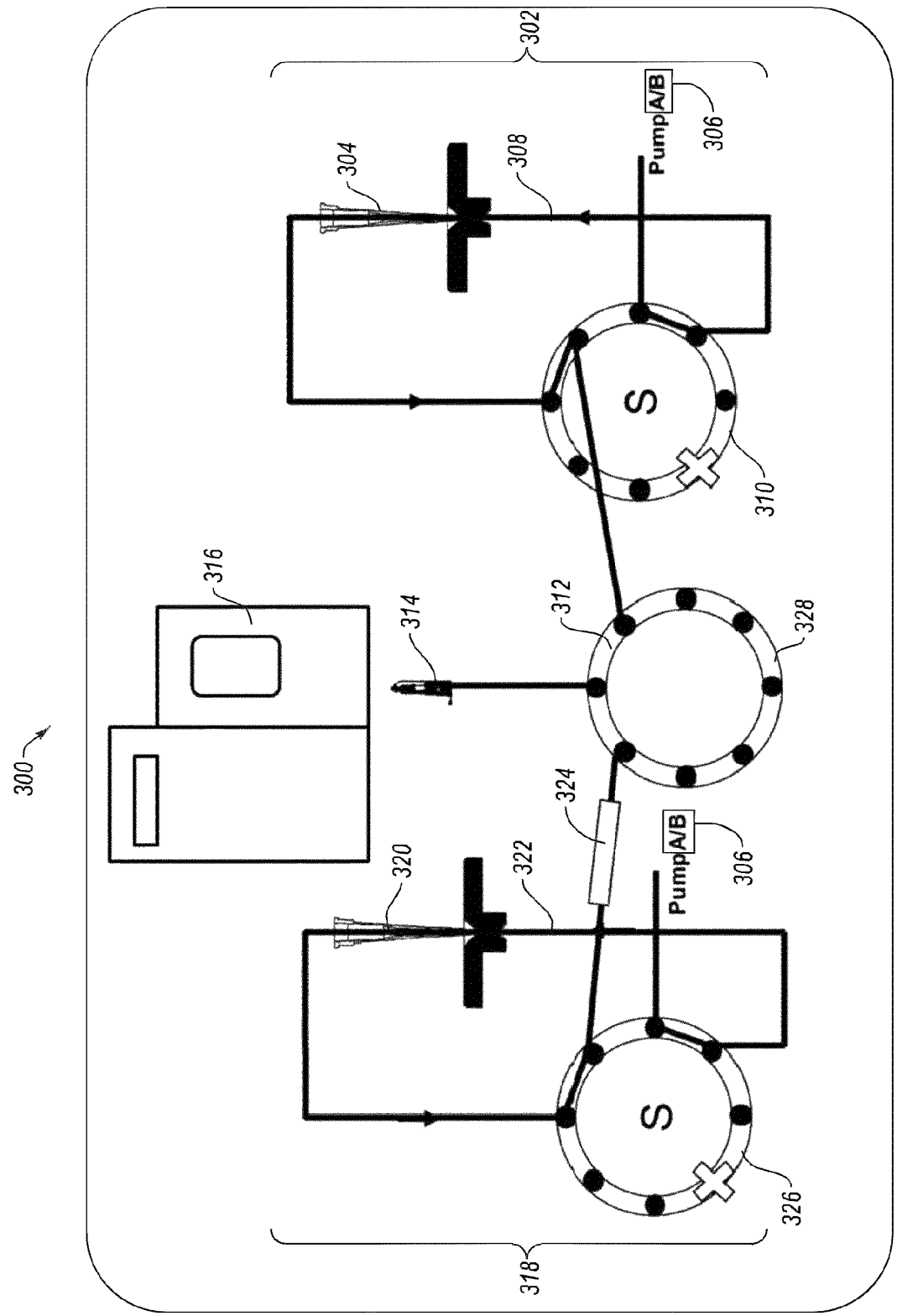
FIG. 3 is a diagram schematically illustrating a flow path that can be used according to one embodiment in the system illustrated in FIG. 2.

The supernatant produced by disruption of the microorganisms in step 102 contains intact proteins that may be further processed to desalt and concentrate the proteins, as illustrated in step 104 of FIG. 1A. In one embodiment, an automatic solid phase extraction/liquid chromatography sample introduction interface system is used to simultaneously desalt, concentrate and separate the intact proteins. A schematic diagram of such a system 300 is shown in FIG. 3. In a first flow path 302, the system 300 may employ a single-use disposable solid phase extraction (SPE) cartridge 304 that is coupled to a pump 306, fluid lines 308, a first switching valve 310, a second switching valve 312, and an electrospray ionization (ESI) emitter 314. The SPE cartridge 304 may be conditioned, for example, using a 2% acetonitrile/0.2% formic acid aqueous solution (loading buffer). Next the sample prepared in step 102 of FIG. 1A may be loaded from substantially the same solution and passed through the SPE cartridge 304 using, for example, reverse flow. The SPE cartridge 304 may then be washed with 2 bed volumes of the loading buffer to remove salts and other contaminants. After the washing step, each sample is eluted from the SPE cartridge 304 in a solvent volume which may be as small as 10 nl or less or as large as 10's of µl to concentrate and optimize the intact proteins for delivery to the ESI emitter 314 and the mass spectrometer 316.

In one embodiment, the on-line SPE cartridge may be a polypropylene tip with a small volume of silica sorbent containing bonded $C_4$, $C_8$, $C_{18}$ or other functional groups immobilized in the tip, for example, a Stage™ tip (Thermo Fisher Scientific). In alternative embodiments, polymeric sorbents or chelating agents may be used. The bed volume may be approximately 1 µL to 1 ml. The apparatus and method are well suited to the complex samples derived from the microbial cells because each SPE cartridge is used only once, minimizing carryover problems from one sample to another.

III. Ionization, Mass Spectrometry Analysis, Amino Acid Sequence Information As shown in step 106 of FIG. 1A, the sample is then subjected to mass spectrometric analysis. The eluted proteins are ionized, for example, via electrospray ionization (ESI) or other atmospheric or sub-atmospheric pressure ionization techniques that can be readily combined in-line with liquid chromatography. For ESI, proteins accumulate multiple charges based on the number of free N-termini, histidine, lysine, arginine, or other charge carrying amino acids present in the sequence. The resulting mass spectrum reflects the distribution of multiply-charged ions ("charge state envelope") originating from the same protein that appear at different mass/charge (m/z) values. The m/z values are the result of the same analyte acquiring different number of charges from the electrospray ionization process. The distributions of the charge states are amenable for detection via single or multiple stages of high resolution mass spectrometry whether the sample comprises intact proteins and/or their fragments produced via a top-down method. The molecular weight of a protein can be calculated in a variety of ways. This includes simple methods such as looking at spacing between adjacent isotopes of a single charge state, determining or calculating it using the m/z values of several neighboring isotopically unresolved peaks derived from the same protein, and determining the distance in m/z space between those peaks. Other methods for calculating molecular weights include the thrash algorithm and maximum entropy approaches as well.

After ionization the proteins are passed to a mass analyzer for analysis. As shown in steps 108 and 110, the sample is repetitively scanned in full-scan high resolution MS mode within a selected m/z range. In one embodiment, the mass spectrometer is repetitively scanned in the full-scan high resolution MS mode, for example, in a range from m/z 150 to m/z 2000 in approximately one second to provide mass measurement of the intact proteins at a mass accuracy of approximately 5 parts-per-million (ppm), 3 ppm, 1 ppm, or better. In this embodiment, the source parameters are set as follows: spray voltage=4 kV, capillary temperature=270° C. and source temperature=60° C. For the exemplary LC flow rate 400 µl/min, the source sheath gas is provided at the flow rate of 35 (arbitrary units) and auxiliary gas at the flow rate 5 (arbitrary unit), and source temperature=60 C.°. The obtained mass accuracy is sufficient to provide elemental composition information for the protein (e.g., the number of carbon, nitrogen, oxygen, hydrogen, sulfur, or other atoms present in the protein). This information can be further used as part of an algorithm to identify microorganism.

As used herein, the terms "mass accuracy" and "ppm" refer to the degree of conformity of a measured quantity to its actual true value. In the case of measuring the mass, or more specifically the mass-to-charge ratio, of an ion in a mass spectrometric measurement, the difference or error between the experimentally measured mass and the exact mass of an ion is expressed in units of parts-per-million (ppm) according to the equation: ((measured mass−exact mass)/(exact mass))×10^6=mass accuracy in ppm.

The exact mass of an ion is obtained by summing the masses of the individual isotopes of the molecule, including any correction for the charge state of the ion. For example, the exact mass of an ionized water molecule containing two hydrogen-1 atoms, one oxygen-16 atom and carrying a charge of +1 is: ((1.007825+1.007825+15.994915)−0.000549)=18.010016 Daltons. If the measured mass of this ion was 18.010200 Daltons (Da), then the accuracy of that measurement would be: ((18.010200 Da−18.010016 Da)/(18.010016 Da))×10^6=10.2 ppm.

Measurement of the mass of an unknown protein or any protein fragment derived biologically or from MS$^n$ to an accuracy of 5 ppm, or better, reduces the number of candidates found when searching a database of known proteins.

Figure 4:
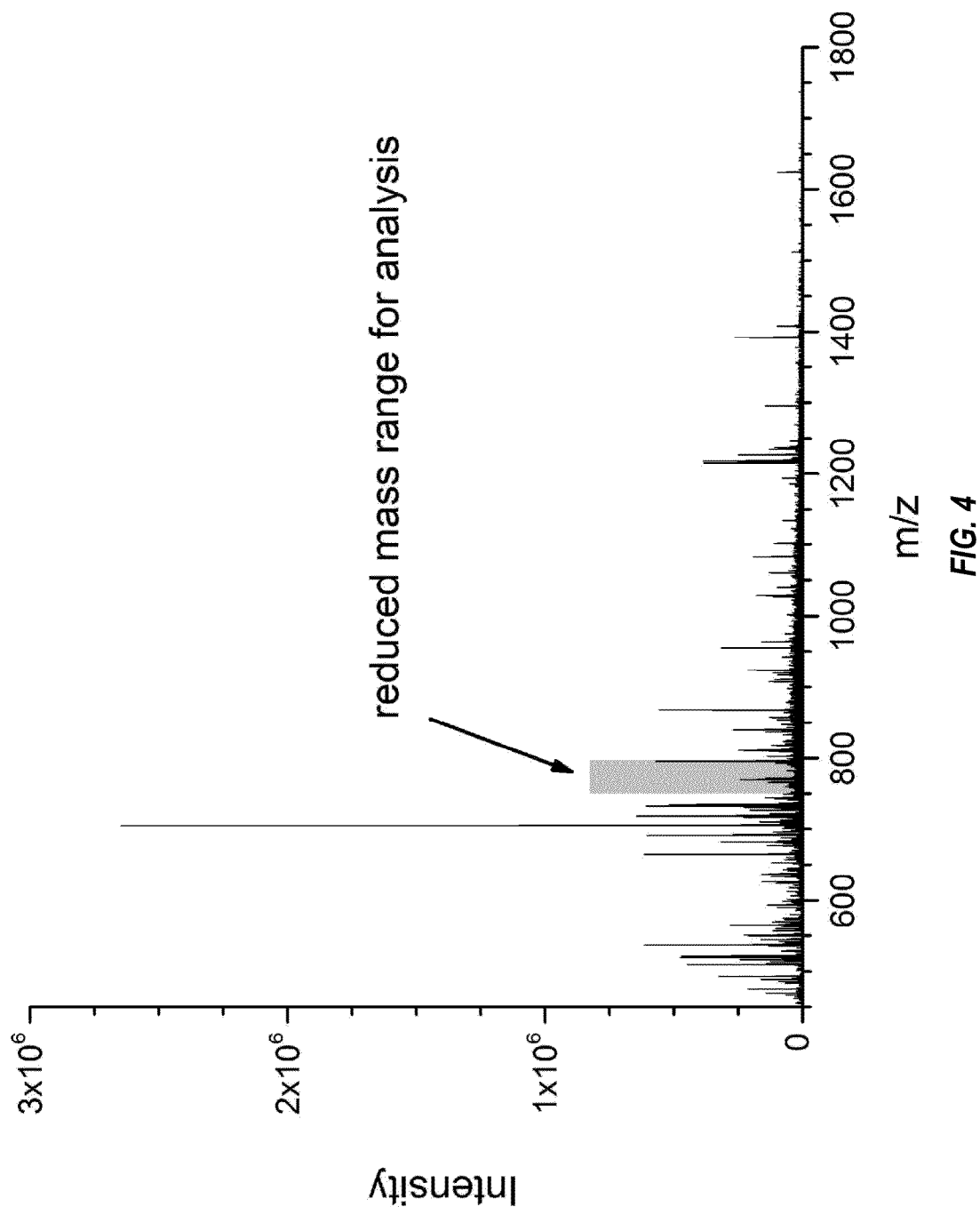
FIG. 4 illustrates a full scan electrospray mass spectrum of an *E. coli* extract performed via direct infusion.

In FIG. 4 a full scan electrospray mass spectrum of an *E. coli* extract performed via direct infusion is illustrated. The scan ranges from m/z 400 to m/z 1800. The extract was obtained as described in this application and was run without any further purification or desalting. The peaks present primarily represent multiply charged mid- and high mass proteins with the exception of some small molecules, small peptides and lipids. This scan provides quality control information that the instrument is functioning properly and the signal is stable for further detailed analysis. Total time of analysis is one second.

Figure 5:
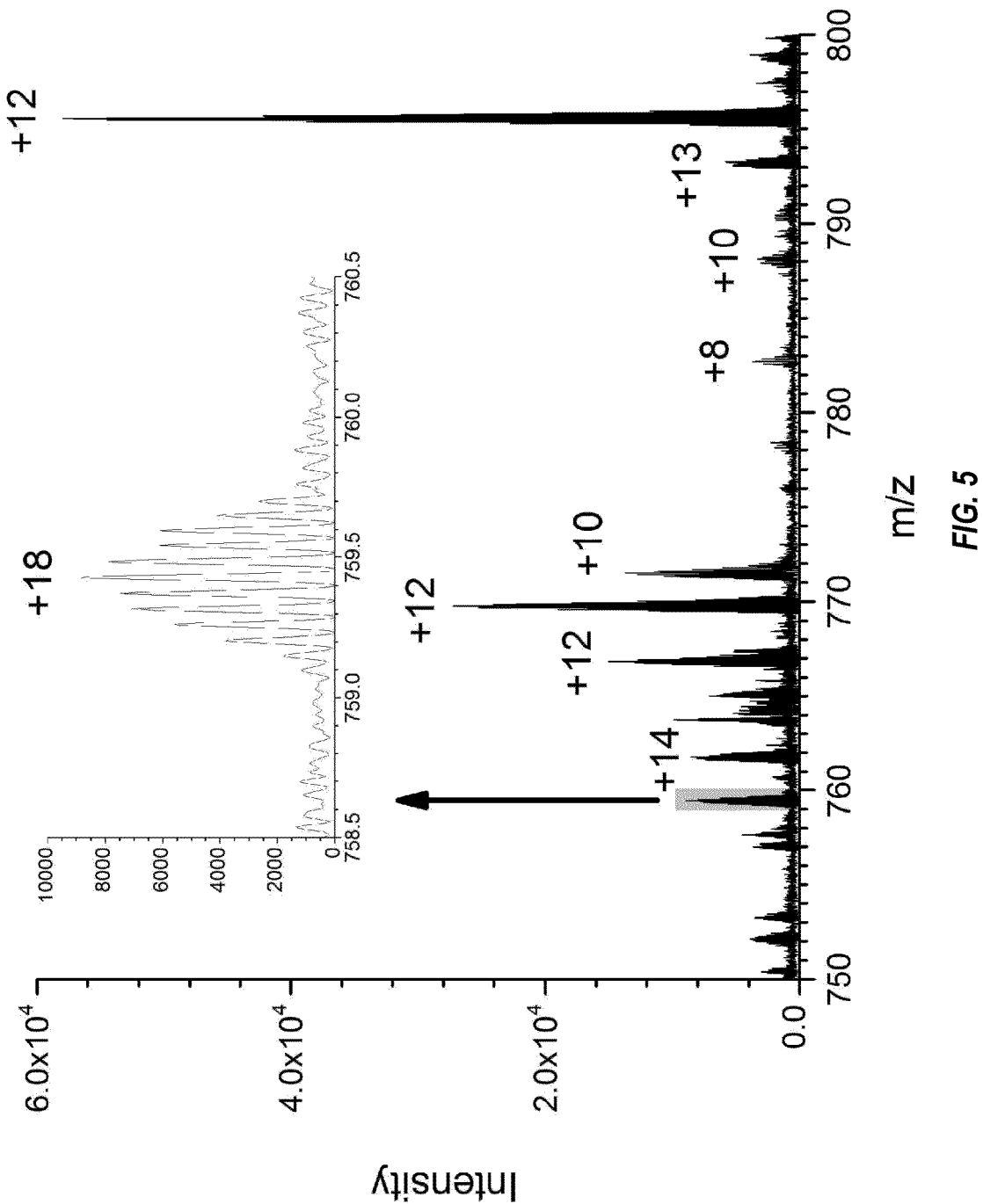
FIG. 5 illustrates a mass isolation of a 50 Da window of the *E. coli* extract shown in FIG. 4.

Mass isolation of a 50 Da window indicated in FIG. 4 is shown in FIG. 5. The mass range scanned is from m/z 750 to m/z 800. Present in the figure are more than nine isotopically resolved peaks representing different charge states of nine different proteins at the following m/z values: 759.4283 (+18), 761.7664 (+14), 766.8419 (+12), 769.7618 (+12), 771.5050 (+10), 782.8381 (+8), 788.1067 (+10), 793.2172 (+13), and 795.5254 (+12). These charge states are then converted to molecular weight values based on the charge state specific isotope spacing. This yields the following molecular weights: 13651.71, 10735.79, 9190.10, 9237.14, 7705.05, 6254.70, 7871.07, 10311.82, and 9546.30. These molecular weights can be searched against the pathogen molecular weight database in real time in order to retrieve a reduced number of potential pathogen identifications. For example, 50S ribosomal protein L27, nucleoid associated protein YbaB, 50S ribosomal protein L17, integration host factor subunit b, 30S ribosomal protein S16, uncharacterized protein YehE, and r50S ribosomal protein L31 were tentatively identified from this search where the input data originate from high resolution mass spectrometry that delivers very high measurement mass accuracy.

The identification process can occur in real time during the data acquisition or post acquisition. The data acquisition process defined in step 110 of FIG. 1A can include the direct infusion of the protein extract or flow injection combined to SPE clean-up as described in this application. The key component here is matching calculated molecular weight obtained experimentally with those in the microorganism/pathogen database. When the identification process occurs during the data acquisition period, the highly accurate molecular weight information obtained for a defined acquisition window is matched against the highly accurate molecular weight microorganism/pathogen database. This effectively reduces the number of possible microbial identifications candidates in real time (in several seconds).

In another embodiment of the invention, proteins are analyzed not only by their molecular weight, as described above, but also using the data on their unique amino acid sequences which are then compared to a reference database that contains known amino acid sequences of microbial origin. In this embodiment, molecular weights of intact proteins are determined, and protein sequence information is obtained via multi-stage mass spectrometry. This is illustrated in step 112 of FIG. 1A. Using the molecular weights determined in steps 108 and 110 allows for the follow on step of tandem mass spectrometry to unequivocally identify the microorganism/pathogen of interest. Molecular weights can be calculated directly from distances between the isotopes in isotopically resolved peaks, or by determining the centroid and m/z spacing for very high mass proteins (peaks are not isotopically resolved) as the data acquisition progresses.

Typically, a selected charge state of a protein is mass isolated and excess energy is deposited to a protein precursor ion population in order to induce the formation of sequence specific fragment ions as a result of collisions with an inert gas (atomic or molecular) or by other methods known in the art. This energy deposition process may be derived from low or high energy collisional activation (CA) dissociation event, the absorption of infrared photons via infrared multiple photon dissociation (IRMPD), the absorption of a single UV photon, through ion-ion reactions including electron transfer dissociation (ETD) or collisional-activation of electron transfer product ions which do not undergo prompt fragmentation, electron capture dissociation (ECD), or other.

In an exemplary embodiment, the dissociation method is low or high energy collision-induced dissociation (CID) where normalized collision energy ranges from 5 to as high as 50 percent (normalized collision energy, arbitrary units). Precursor ions are typically automatically selected from the most intense peak in a charge state distribution derived from any given protein.

Figure 6:
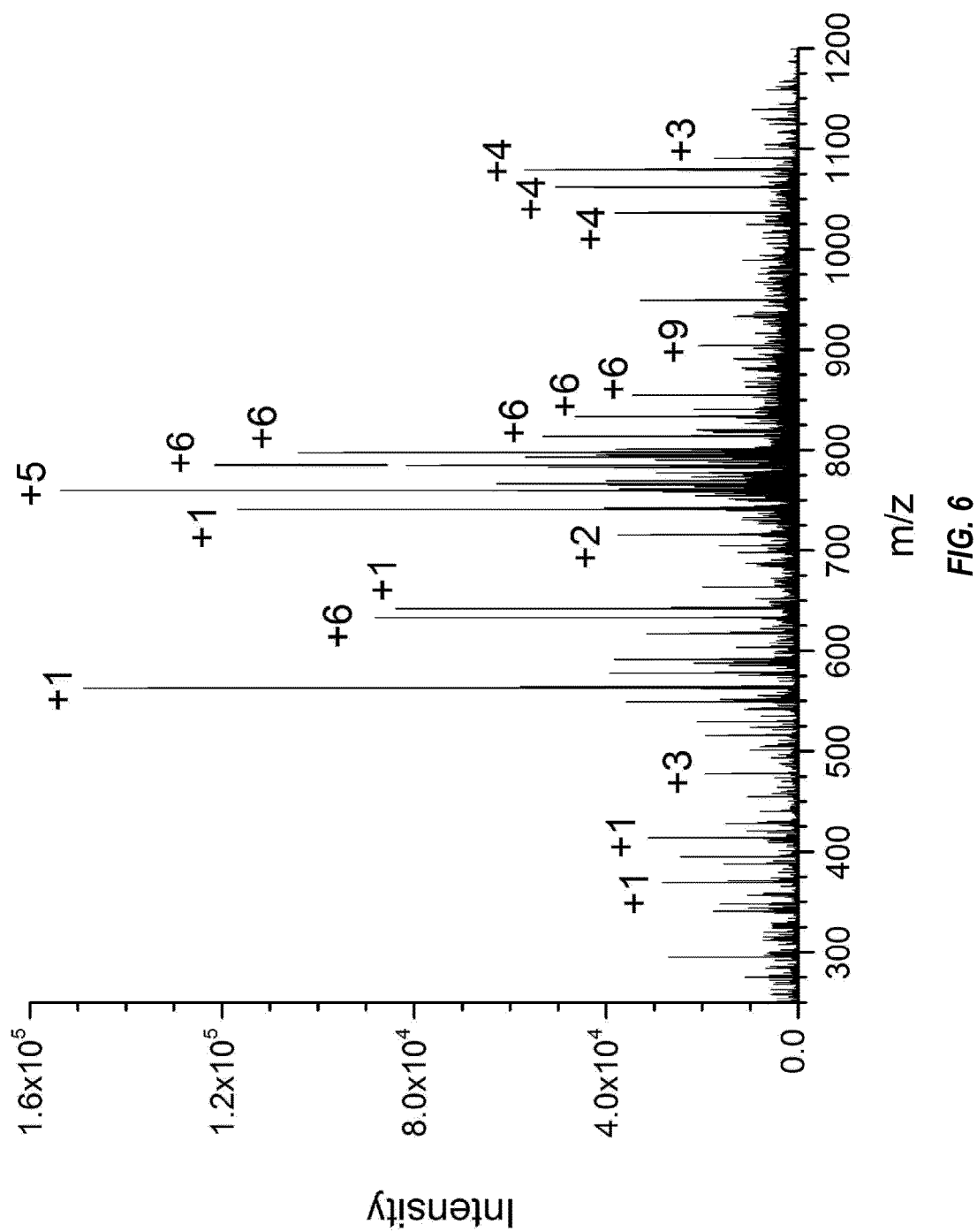
FIG. 6 illustrates tandem mass spectrometry of the 50 Da window illustrated in FIG. 5.

FIG. 6 illustrates a tandem mass spectrometry scan of the of the 50 Da window from m/z 750 to m/z 800 described above with respect to FIGS. 4 and 5. All precursor ions listed in FIG. 5 were subjected to collision-induced dissociation (CID) via the HCD cell on a Q Exactive high resolution/mass accuracy mass spectrometer. The normalized collision energy was set to 18% with a resolution of 35,000. The resulting fragment ions produced ranged in charge state from +1 to +9 for the thirty most prominent peaks. These peaks correspond to fragment ions derived from a representative set of labeled (via charge state) precursor ions shown in FIG. 5. These fragment ion identities are then matched to the precursors listed above but can be associated with precursor ions with very low signal-to-noise ratios. This matching process also occurs in real time and is used to narrow the identification of the pathogen to E. coli.

However, in one embodiment of the invention the more highly charged state ions of a given protein are chosen to undergo CID. This is supported by the data shown in FIG. 7. Here the resulting product ions are obtained as a resolution of 35,000 with a mass accuracy of 3 ppm or better. The protein shown was identified as DNA Binding Protein H-ns from a resistant E. coli strain grown in the presence of ampicillin. The method of collision-induced dissociation (CID) was used to fragment the intact protein at a precursor m/z value of 811.9018 (+19 charge state, approximate molecular weight 15.4 kDa). By selecting this precursor ion, the resulting fragments (b-y series ions) derived from the intact protein can be identified via preferential cleavage sites. In this example, the m/z values 813.82440, 904.13885, and 1017.03210 are $b_{70}$ ions that cleave between an aspartic acid (D) and proline residue (P). Other prominent peaks at m/z 742.90741 and 1077.57056 cleave on the C-terminal side of glutamic acid (E) to produce $b_{26}$ and $b_{27}$ ions. The fragment matching portion of the algorithm preferentially weights more intense fragment ions to accurately identify the protein quickly. By combining this information with the molecular weight of the intact protein, protein can be identified and pathogens can be identified at to the species level and, in many cases the strain level.

Figure 7:
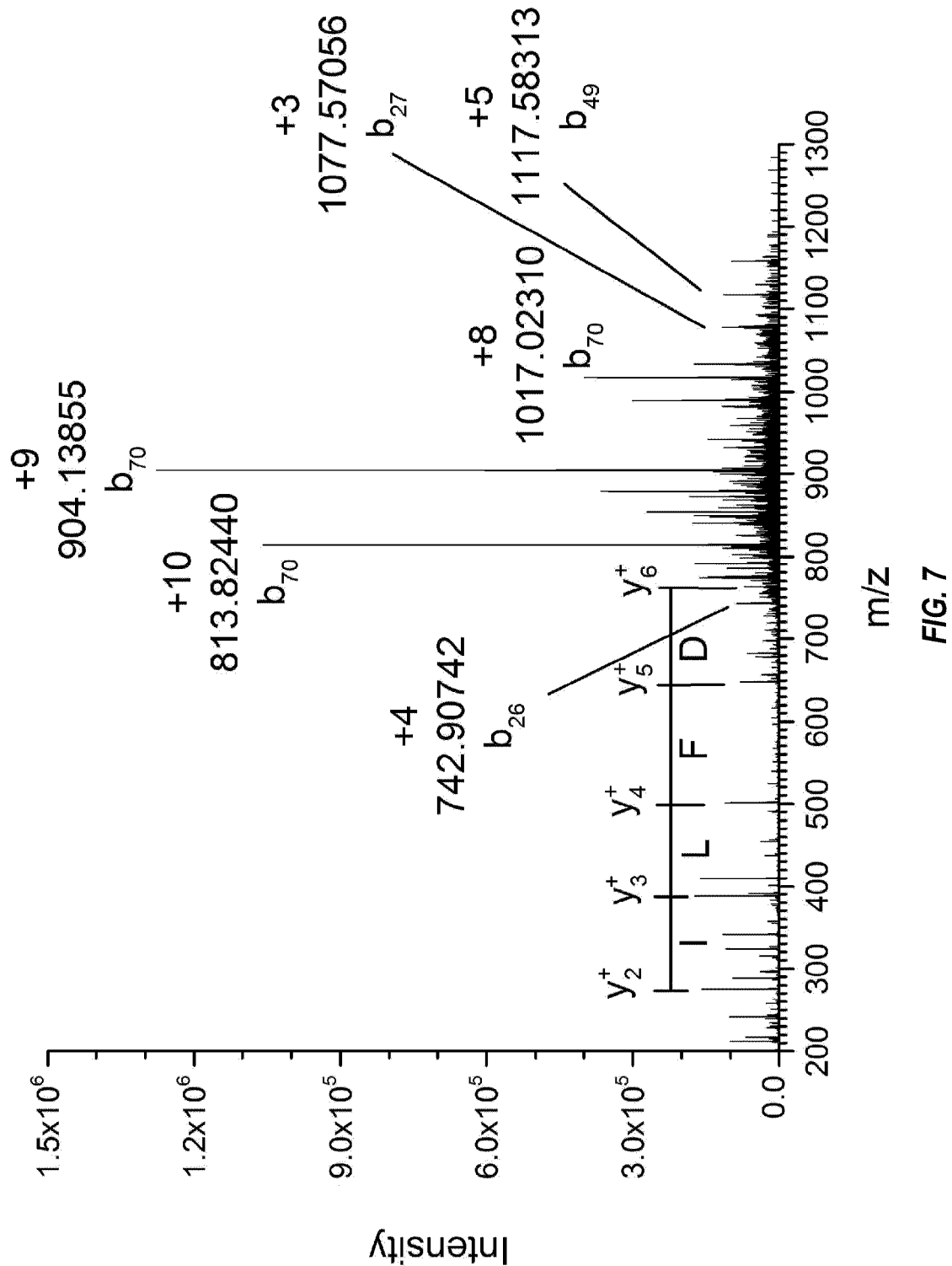
FIG. 7 illustrates an MS/MS fragmentation of the +19 charge state of DNA Binding Protein H-sn from *E. coli*.
Figure 8A:
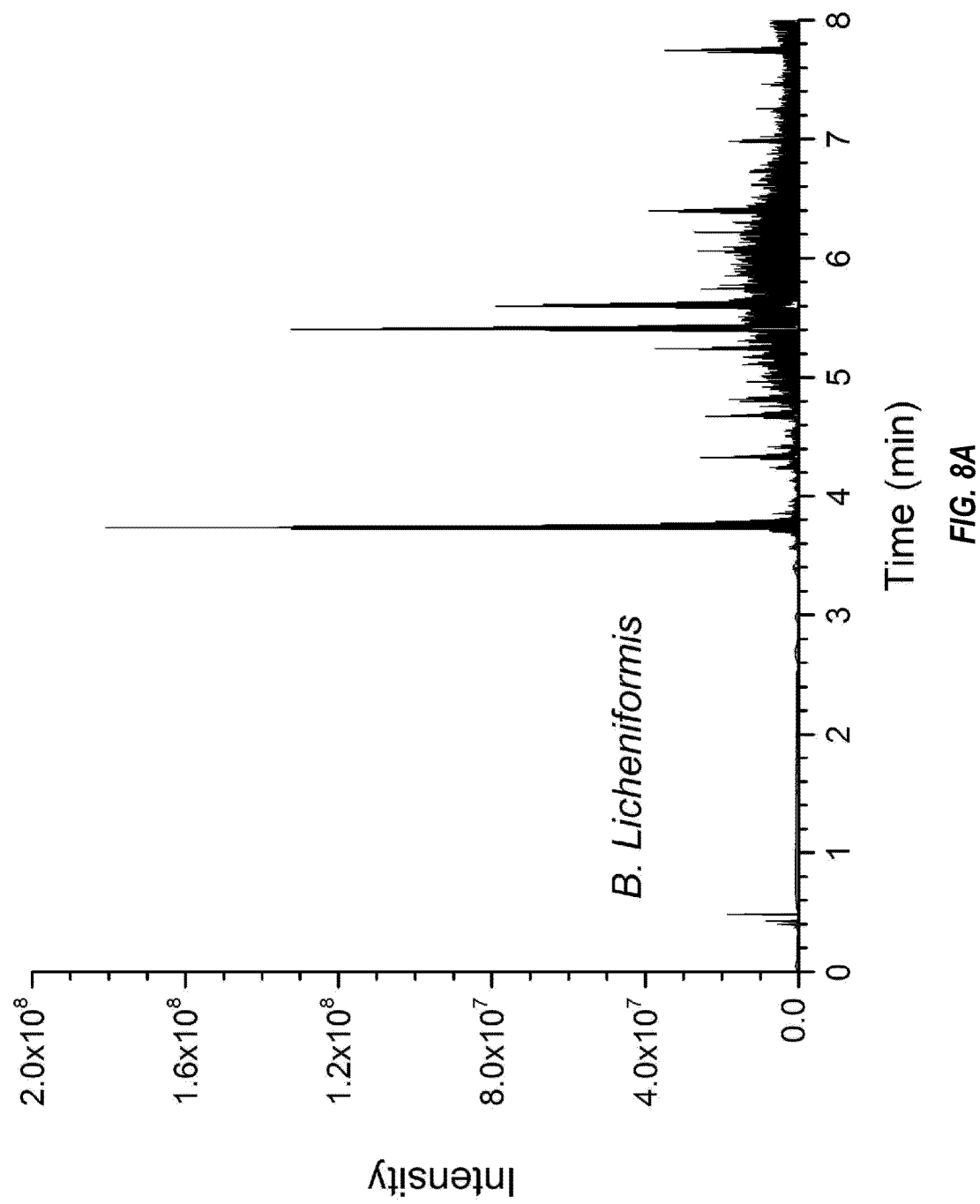
FIGS. 8A-8E illustrate mass spectrometry data for fast partial chromatographic separation of soluble proteins extracted from *Bacillus licheniformis*, *Candida albicans*, *Kocuria rosea*, *Staphylococcus xylosus*, and *Mycobacterium smegmatis*.
Figure 8B:
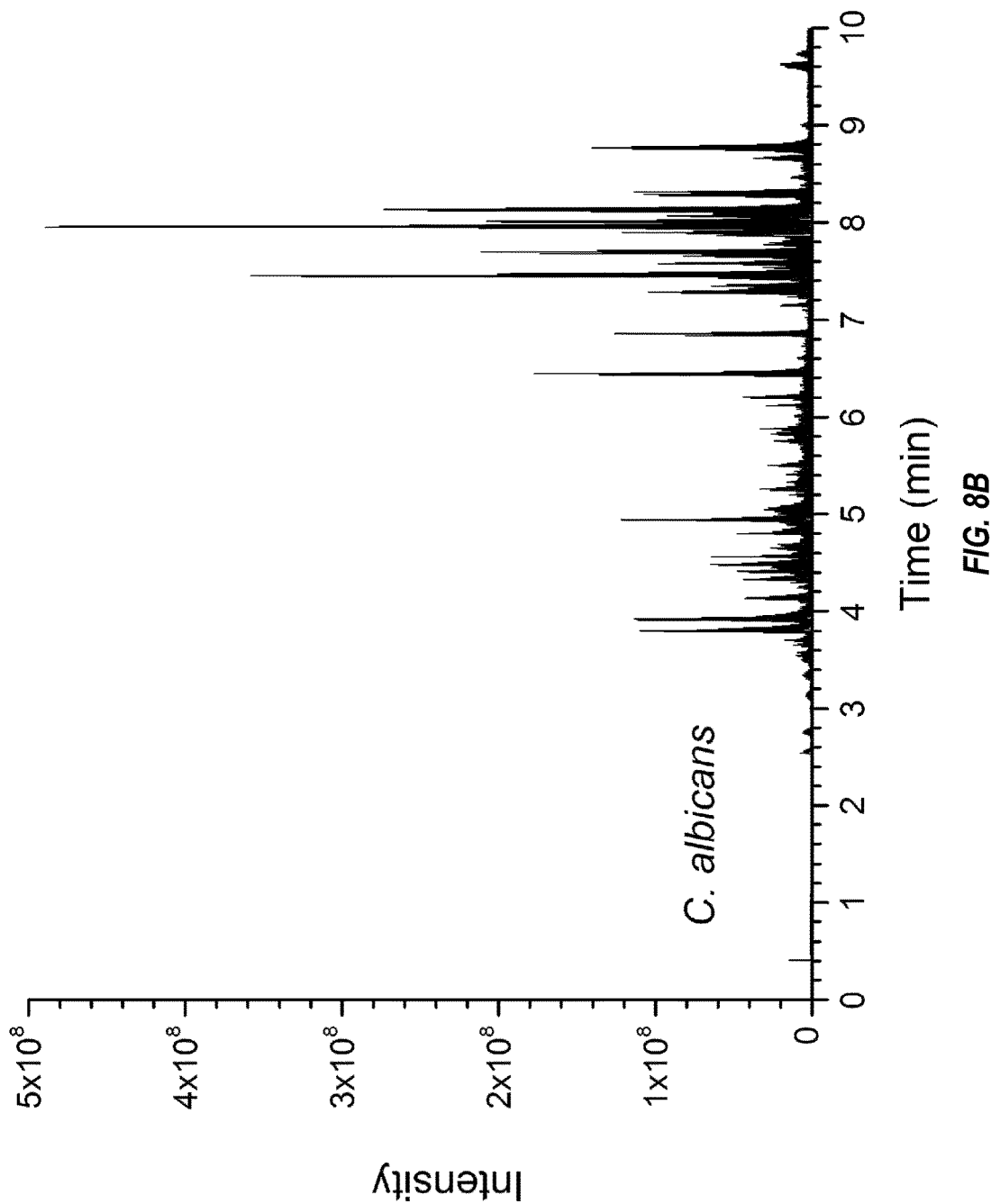
Figure 8C:
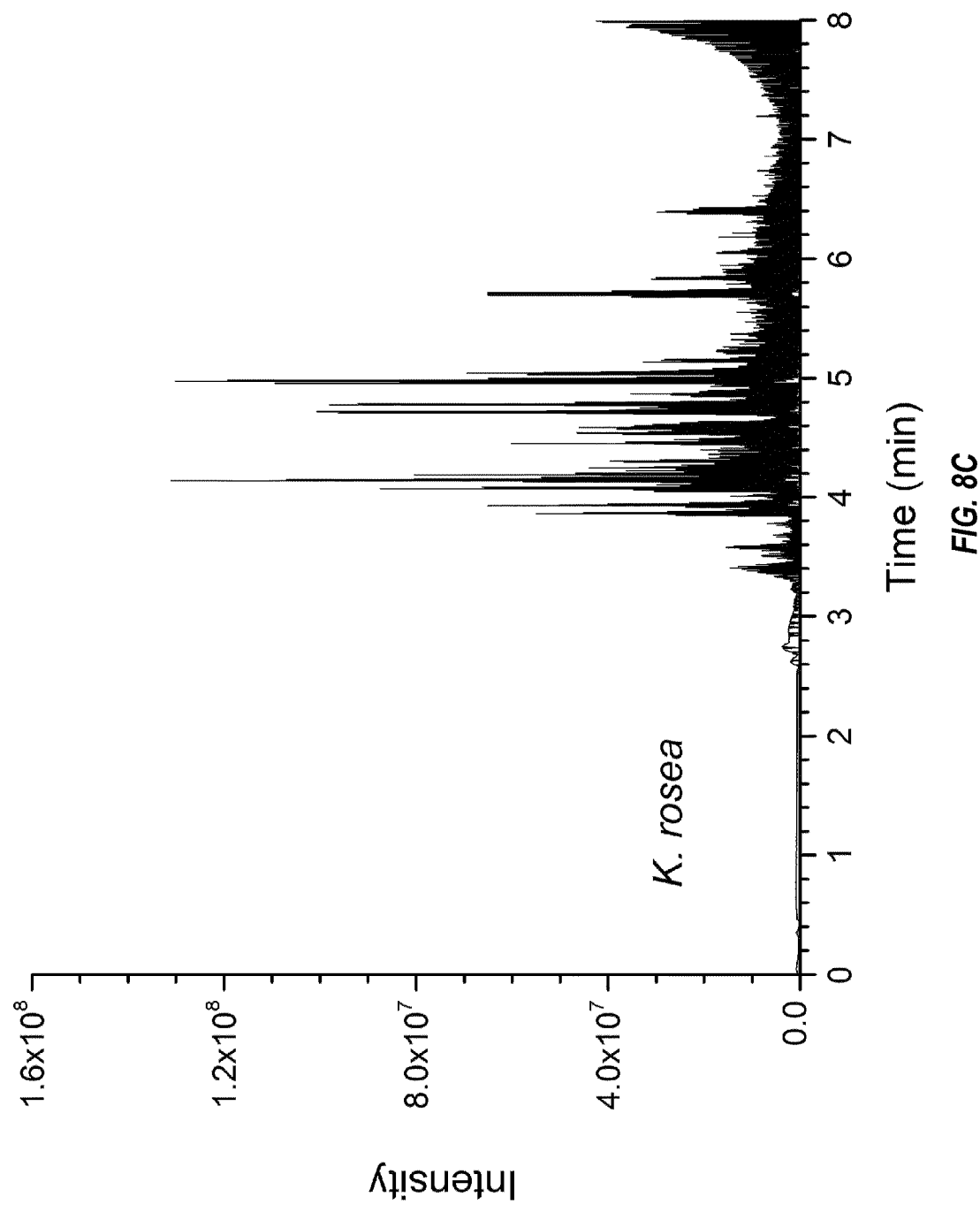
Figure 8D:
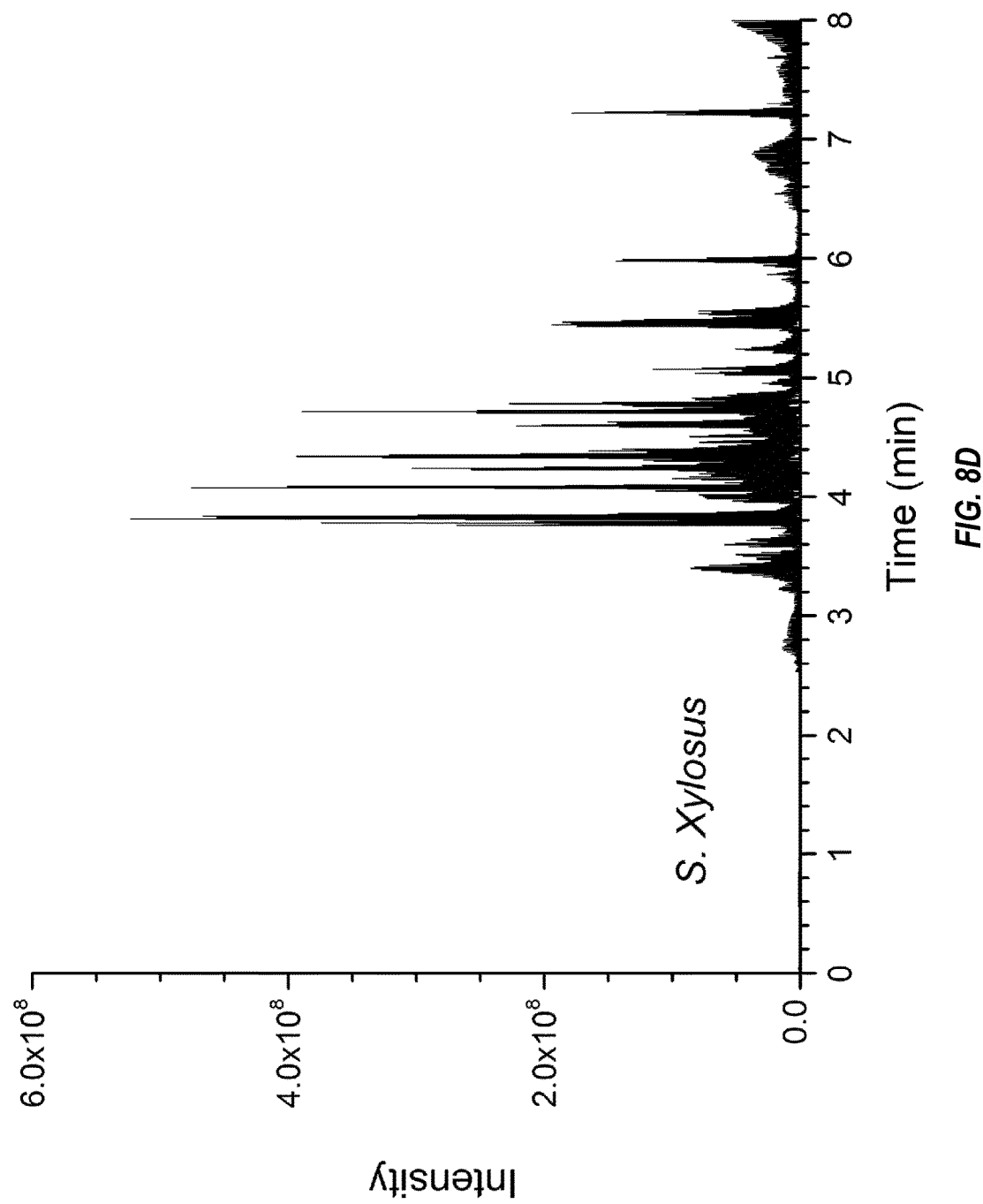
Figure 8E:
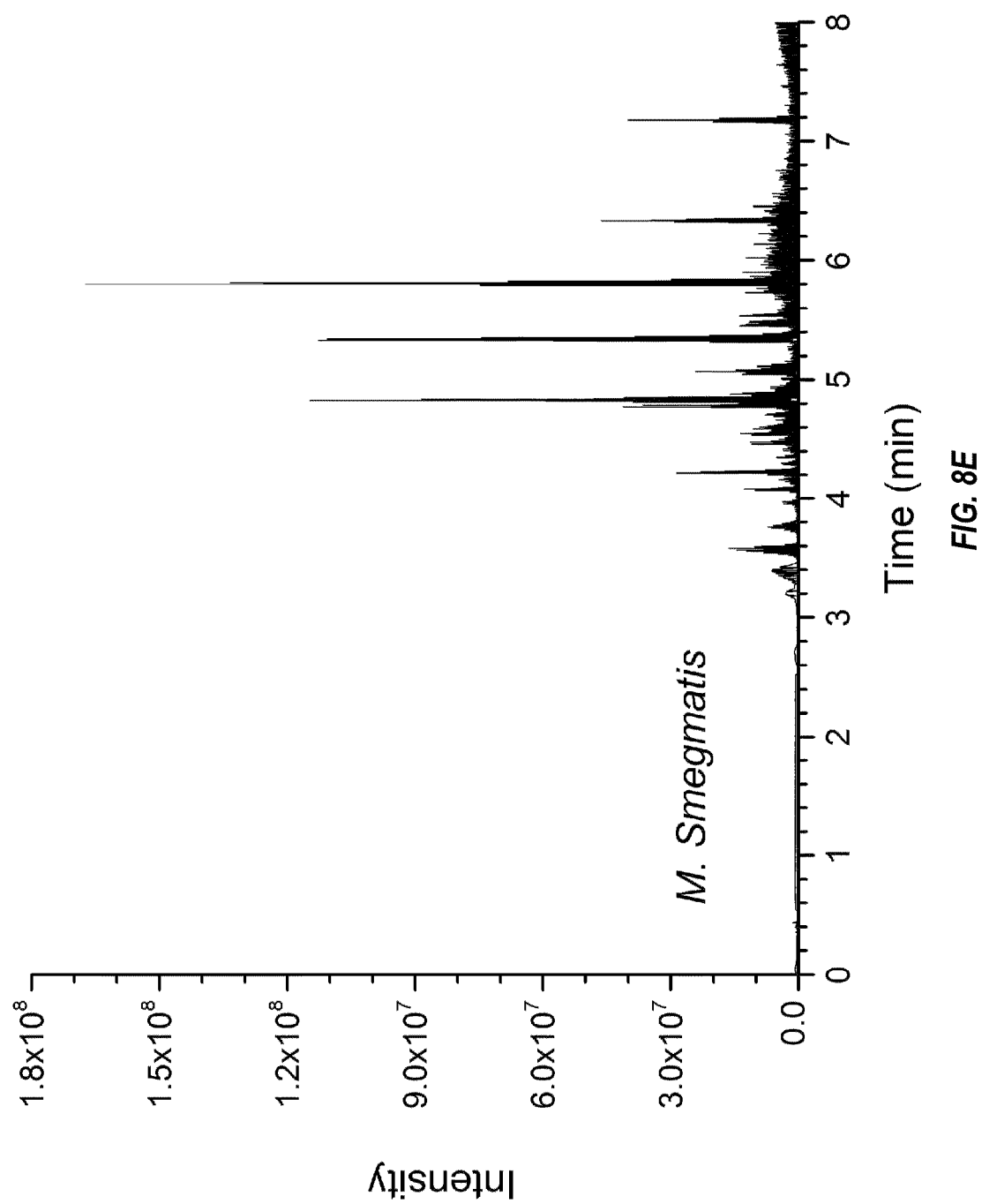

In one embodiment, sequence tag information may also be generated to confirm the identification of the protein. A computer software program examines the product ion mass spectrum for obvious sequence tags. A sequence tag is a short string of two or more amino acids deduced by mass differences between major fragment ions in the product ion mass spectrum. The sequence tag and its location in the peptide or protein relative to the amino and carboxyl terminus are used as constraints in the database search. Used in combination with molecular weight, sequence tag information provides for identification of proteins with high confidence. Since many proteins produced in prokaryotic and eukaryotic cells undergo loss of N-terminal methionine, signal peptides, or other post-translational modification events, calculations are used to account for these modifications. This principle is also illustrated in FIG. 7. FIG. 7 illustrates a series of singly-charged y-type ions which correspond to the sequence tag I/L I/L F D. This in combination with the molecular weight at 15.4 kDA can be used to identify the protein. In addition, the most intense fragments observed are those where cleavage occurs on the C-terminal side of aspartic (D) and glutamic acid (E) and the N-terminal side of proline (P). These preferential cleavages typically observed in the CID mass spectrum of proteins can be used to speed up the database search process by weighting these peaks based on intensity.

Additionally, programs such as ProSight PTM, MS-Align, UStag, MS-TopDown, PIITA, and OMMSA (Open Mass Spectrometry Search Engine) can be used to identify intact proteins derived from top-down mass spectrometry experiments. Smaller peptide and protein fragments upon mass analysis of the corresponding product ions are identified via one of several different database search engines including correlation based (Sequest), probability based (Mascot), expectation value calculation programs (!Xtandem), or other approaches know in the art. Protein identifications from the aforementioned methods are then used to identify the genus, species, subspecies, strain and/or serovar of the organism. The same protein identification workflow method can be applied to proteins specific to virulence factors, resistance markers, and other relevant markers.

In another embodiment of the invention, tandem mass spectrometry is used to generate fragment ions of the peptide or protein, and the resulting spectrum is matched against a multi-stage mass spectrometry reference database to identify the organism. Such database may also include chromatographic retention time information, mass of the protein including any posttranslational modifications, mass of the peptide or protein fragments, elemental composition (C, H, N, O, S or other atoms), general peak intensity or intensity as it relates to preferential cleavage, and sequence tag information derived from known microorganisms.

IV. Data Analysis and Identification to Genus-Species Level

Any one or more of chromatographic retention time, mass, intensity, elemental composition, amino acid composition, and protein sequence information may be used to identify the microorganism(s) present in the sample. Identification is based on MS and $MS^n$ data and any of the aforementioned parameters compared to a known reference database(s). Chromatographic retention time may be absolute, as measured using a defined column and set of chromatographic conditions to separate the components or group of the components of the sample, or may be relative to the retention time of some other component or components present in or added to the sample being analyzed.

The steps of an algorithm for providing an initial ID for an unknown microorganism in a sample may be performed in less than a minute. The identification process can occur in real time during the chromatographic separation and data acquisition or after data acquisition and/or chromatographic separation. During the data acquisition period parameters such as retention time, mass-to-charge ratio (m/z), and intensity information is stored in the systems on-board memory. When the identification process occurs during the chromatographic separation/data acquisition step, raw data is processed in real time based on the principles of MS/MS (tandem mass spectrometry) as well as molecular weight matching by an identification algorithm. An identification algorithm involves matching the experimental peaks based on retention time, mass, elemental composition, amino acid frequency, and intensity to a reference database. Once enough data has been acquired to identify the microorganism(s) of interest, confirmation of identification and/or detection of virulence factors and resistance markers may be performed. For the MS/MS process, confirmation peaks are chosen in real time based on the identification of the microorganism. The MS/MS process occurs automatically and the results are searched against a MS/MS database, which contains sequence information for known microorganisms.

Alternatively, peaks can be directly identified using another algorithm. The same principle applies to the confirmation of virulence factors or resistance markers for a particular organism. Once all data is acquired, MS-based information and MS/MS-based protein/microorganism identification information are updated in real time and are used in a scoring process performed using an algorithm specifically developed for such purpose.

Figure 1B:
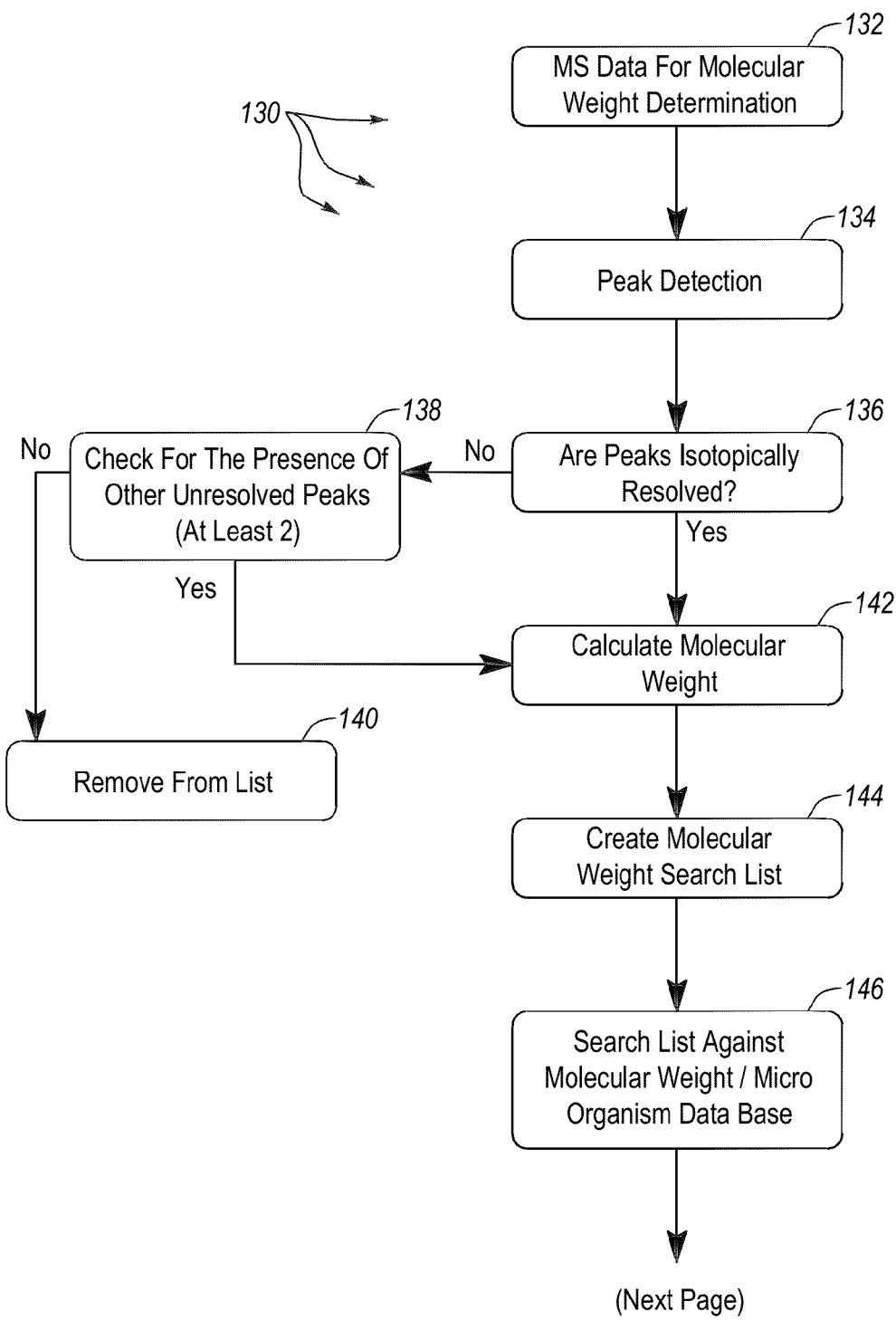
FIG. 1B is a flow diagram schematically illustrating an algorithm for identifying a microorganism.
Figure 1B:
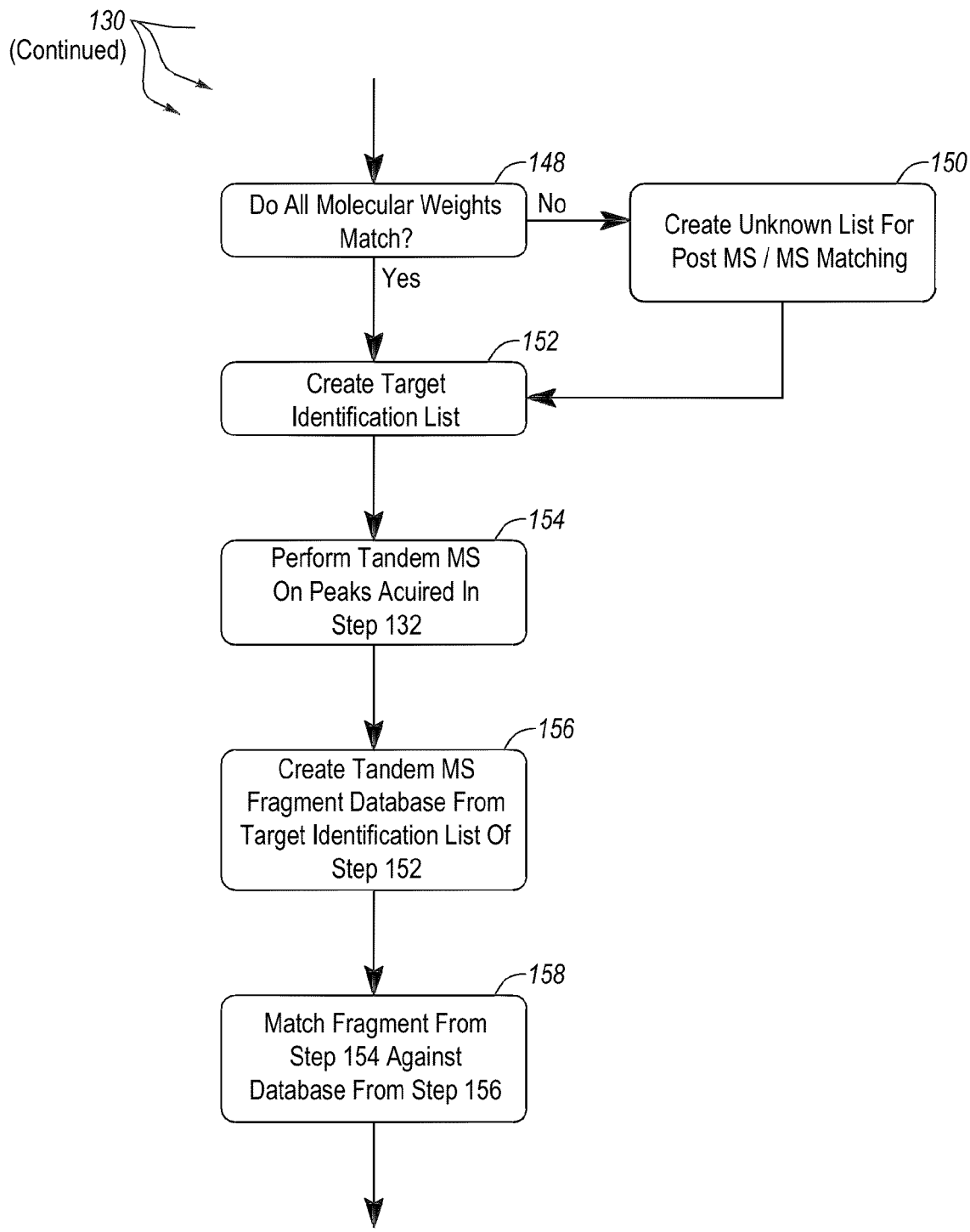
Figure 1B:
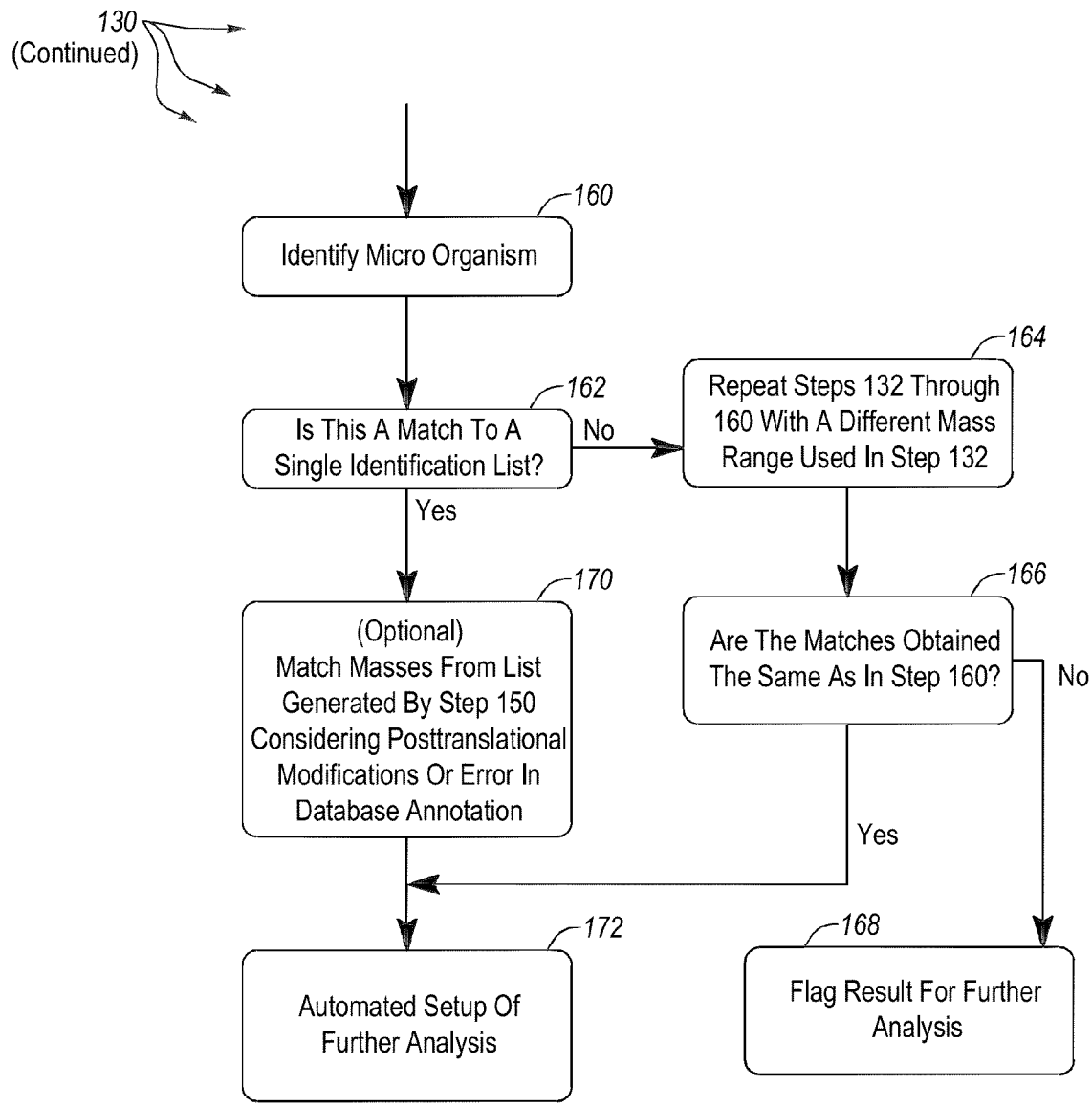

Referring now to FIG. 1B, one example of a suitable algorithm 130 that can be used to identify a microorganism based on the data obtained in steps 102 through 112 (see FIG. 1A) and steps 110 and 112 (See FIG. 1A) in particular is illustrated. The algorithm includes a step 132 of obtaining mass-spec data for molecular weight determination. This may be done in step 110 of FIG. 1A. The algorithm then includes a step 134 of peak detection, a step 136 of determining whether any of the peaks are isotopically resolved. If the peaks are isotopically resolved, the algorithm calculates the molecular weight associated with the peaks in step 142. If the peaks are not isotopically resolved, the algorithm then includes a step of checking for the presence of other unresolved peaks that can be assigned to the same charge state envelope. If there are additional peaks, molecular weight can be calculated according to step 142. If there are no additional peaks in the same mass spectrum, the algorithm looks for the candidates in the mass spectra that show the adjacent mass ranges. If the peaks are not found, the original peaks are removed from the analysis in step 140.

Based on the calculated molecular weights (step 142), the algorithm 130 may then create a molecular weight search list (step 144) and search the molecular weight search list against a molecular weight/microorganism database (step 146). The algorithm 130 then asks whether or not all of the molecular weights match in step 148. If the molecular weights do not match, the algorithm 130 creates an unknown list for post MS/MS matching (step 150) and creates a target identification list (step 152). If the molecular weights do match, the algorithm creates a target identification list (step 152).

The algorithm 130 is capable of using the information derived about the molecular weights of the protein in the sample derived in the previous to perform subsequent analysis to refine the assignment of the identity of the organism. In step 154, the algorithm may direct the mass-spec instrument to perform a tandem mass-spec on the peaks acquired in step 132. The algorithm then directs the creation of a tandem MS fragment database from the target identification list of step 152 in step 156, and then in step 158 match the fragments from step 154 against the database from step 156. These data (steps 152 and 158) are used to identify the microorganism in step 160.

The algorithm 130 then checks whether or not this is a match to a single ID in step 162. If there is a single match in step 162, the algorithm 130 then includes an optional step of matching masses from the list generated in step 150 against possible post-translational modifications and/or errors in the database annotation. The sample may be submitted for further analysis as described herein below as illustrated in step 172. If the match in step 162 is not to a single ID, the algorithm then repeats steps 132 through 160 with a different mass range used in step 132. If the match is the same as obtained in step 162, then the sample may be submitted for further analysis as described herein below as illustrated in step 172. If the match is not the same as obtained in step 162, then the sample may be flagged for further analysis (step 168).

All processes of identification may be fully automated and occur in the background of a given data acquisition process. Alternatively, these steps can occur post acquisition as well. The results of microorganism identification may be provided in a user friendly format, for example, to a remote device, a mobile device and/or a centralized computer system, which can be pre-selected prior to sample processing.

Alternative approaches may be used to match high resolution/mass accuracy ESI data to the spectra in reference databases. Such methods include, without limitation, linear, randomized, and neural network pattern match based approaches. Electrospray ionization allows a greater number of proteins from any given organism to be detected, so that the specificity of the pattern match based approach is greatly improved over MALDI-based techniques. The increased information content available with the LC-MS and MS/MS based approach of the present invention allows for a more detailed characterization of the microorganism at the strain or subspecies level and can minimize the false positive rate. For example, the presence of two or more different species, strains, or subspecies in a single sample has presented a challenge to previous analyses based upon MALDI-TOF mass spectrometry. An advantage of the combined MS and MS/MS (MS") approach of the present invention is that any unique protein may be used to check the accuracy of identification. A database may include information regarding species capable of unequivocal identification based upon presence of a single protein. Species requiring further checks can be analyzed independently.

B. Targeted Analysis of Specific Characteristics

When identification at the genus/species level is accomplished, the sample may optionally be reanalyzed for detailed information including, without limitation, information relevant to typing (strain and/or serovar), virulence, or antibiotic resistance and/or susceptibility. This second analysis (re-analysis) may be targeted for one or more specific proteins based upon the identity or identities of the microorganism(s) identified during the first analysis. This is indicated in FIG. 1A by arrow 114, which shows information from the first analysis being used to direct the second analysis.

Based upon the genus or species identification obtained from the sequence of events in steps 104 through 112 of FIG. 1A, the instrument software may use programs coded with the Instrument Advanced Programming Interface (IAPI). The IAPI software (Thermo Fisher Scientific) is a data acquisition directing master control program that allows the programming of the logics of making decision for the next acquisition steps in real-time while the sample is still being analyzed and the analyte is still readily accessible for further analysis. The software is .NET compatible event driven software that virtually adds no overhead time to the analysis. Since the software system has asynchronous control, multiple "listeners" can respond to s single event or trigger. Any variety of computer language can be used including all derivative of the C programming language, visual basic, and Python just to name a few. As an example, the software is used to drive the molecular weight database reduction process that is described earlier and is performed during data acquisition. In this section is described the methodology for triggering a selective experiment for typing, virulence detection, and resistance marker identification.

As an example for the case of pathogenic *E. coli*, the software can immediately set up a rapid scan for detection of the appropriate expressed virulence, resistance, or typing markers. For *E. coli* this would include adhesions, invasions, motility/chemotaxis, toxins, antiphagocytic proteins/molecules, and proteins involved in suppressing the immune response. These can be monitored using fast partial separation mass spectrometry (FPCS-MS) and targeted tandem mass spectrometry as described in the following section of this application.

I. Solid Phase Extraction

Referring to step 116 of FIG. 1A, a second injection of soluble proteins extracted from a sample suspected of containing one or more microorganisms (either the same extract used for identification purposes as described above or another extract prepared from the same sample) may be subjected to a second solid phase extraction (SPE) procedure.

Referring again to FIG. 3, for the second SPE procedure, a system 300 may include a second flow path 318 that can be used to couple an SPE cartridge 320 to a chromatography column 324 via a fluid conduit 322, a first switching valve 326, a second switching valve 328, and an electrospray ionization (ESI) emitter 314. The SPE cartridge 320 was described above in connection with step 104 of FIG. 1A. The SPE cartridge 320 is first conditioned, for example, using 100% methanol or acetonitrile or other suitable combination of solvents followed by a 2% acetonitrile/0.2% formic acid aqueous solution (loading buffer). Next the sample is loaded from a substantially identical solution is loaded and passed through the SPE cartridge 320 using reverse flow. The SPE cartridge 320 may then be washed with 2 or more bed volumes of the loading or other LC/MS compatible buffer to remove salts and other contaminants.

After the washing step, the sample may be eluted from the SPE cartridge 320 in a solvent volume which may be as small as 10 nL or less or 10's of µL to concentrate and optimize intact proteins for delivery to the chromatography column. The SPE cartridge is then placed in fluid connection with the chromatography column 324 for fast partial chromatographic separation of the intact proteins derived from the microbial cells.

II. Fast Partial Chromatographic Separation Mass Spectrometry (FPCS-MS)

Referring to step 118 of FIG. 1A, the sample is then subjected to partial chromatographic separation followed with mass spectrometric analyses. Generally, in performing FPCS-MS, a crude extract of microbial cells containing a complex mixture of various organic and inorganic analytes (small organic molecules, proteins and their naturally occurring fragments, lipids, nucleic acids, polysaccharides, lipoproteins, etc.) is loaded on a chromatographic column and subjected to a chromatography. However, instead of allowing a gradient to elute each analyte separately (ideally, one analyte per chromatographic peak), the gradient is intentionally accelerated to the extent that substantially no chromatographic peaks obtained for example approximately 8 minutes or less, and preferably 5 minutes or less instead of a much longer run time that would be required to obtain a baseline separation. Instead, many analytes are intentionally co-eluted from the column at any given time according to their properties and the type of chromatography (reverse phase, HILIC, etc.) used. Partial or incomplete separation may be also accomplished by other methods known to one skilled in the art, including but not limited to the use of mobile phase solvents and/or modifiers that reduce retention of compounds on the column, selection of stationary phase media that reduce retention of compounds on the column (including particle size, pore size, etc.), operation of the chromatographic system at higher flow rate, operation of the chromatographic system at an elevated temperature, or selection of a different chromatographic separation mode (i.e., reversed-phase, size exclusion, etc.).

Since there are substantially no chromatographic peaks across the whole gradient substantially all of the information about the analytes in a mixture is obtained from the mass spectra. Substantially the only relevant information derived from a chromatogram is the time of elution from the column. Each mass spectrum that is recorded represents a "subset" of co-eluting analytes that is then ionized, separated in mass analyzer and detected. Because all co-eluting analytes are ionized at the same time, they are the subject to the known effects of ionization suppression in mixtures that result from but are not limited to: (1) competition for the charge and (2) suppression of the signal from less abundant analytes. Although effects of ionization suppression are generally referred as "undesirable" for many mass spectrometry methods, in FPCS-MS these effects are used for the benefit of the analysis. However, due to the effects of ionization suppression/suppression of "the less abundant" by "more abundant," the signal from a significantly reduced number of proteins is recorded in a mass spectrum.

Figure 11A:
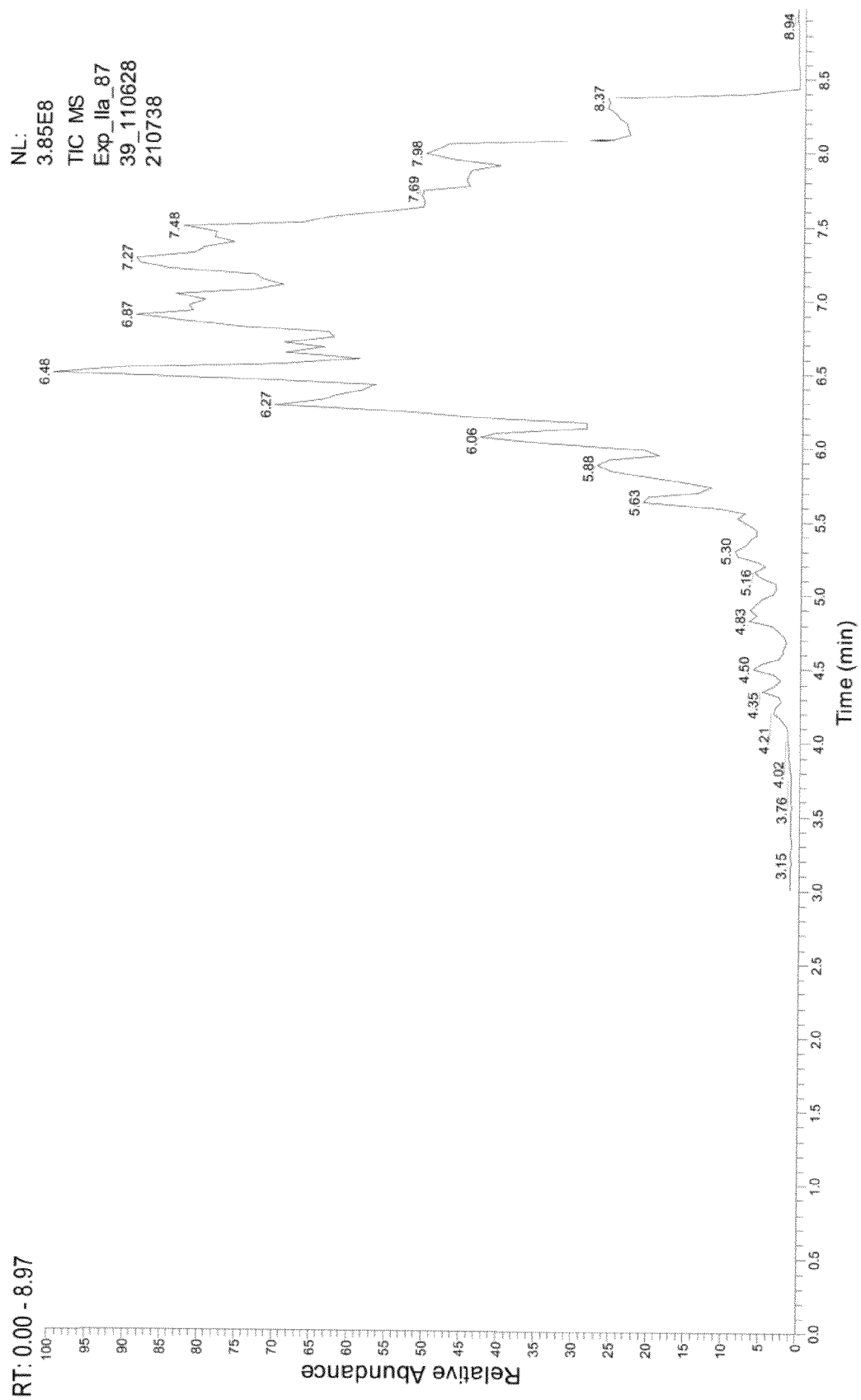
FIGS. 11A-11C illustrate FPCS-MS total ion current profiles of various microorganisms grown on the Oxoid Tryptic Soy Agar at 34 C for 20 h. (A)—*Escherichia coli* ATCC 8739; (B)—*Enterococcus gallinarum* ATCC 700425; (C)—*Bacillus subtilis* subs. *spizizenii* ATCC 6633.
Figure 11B:
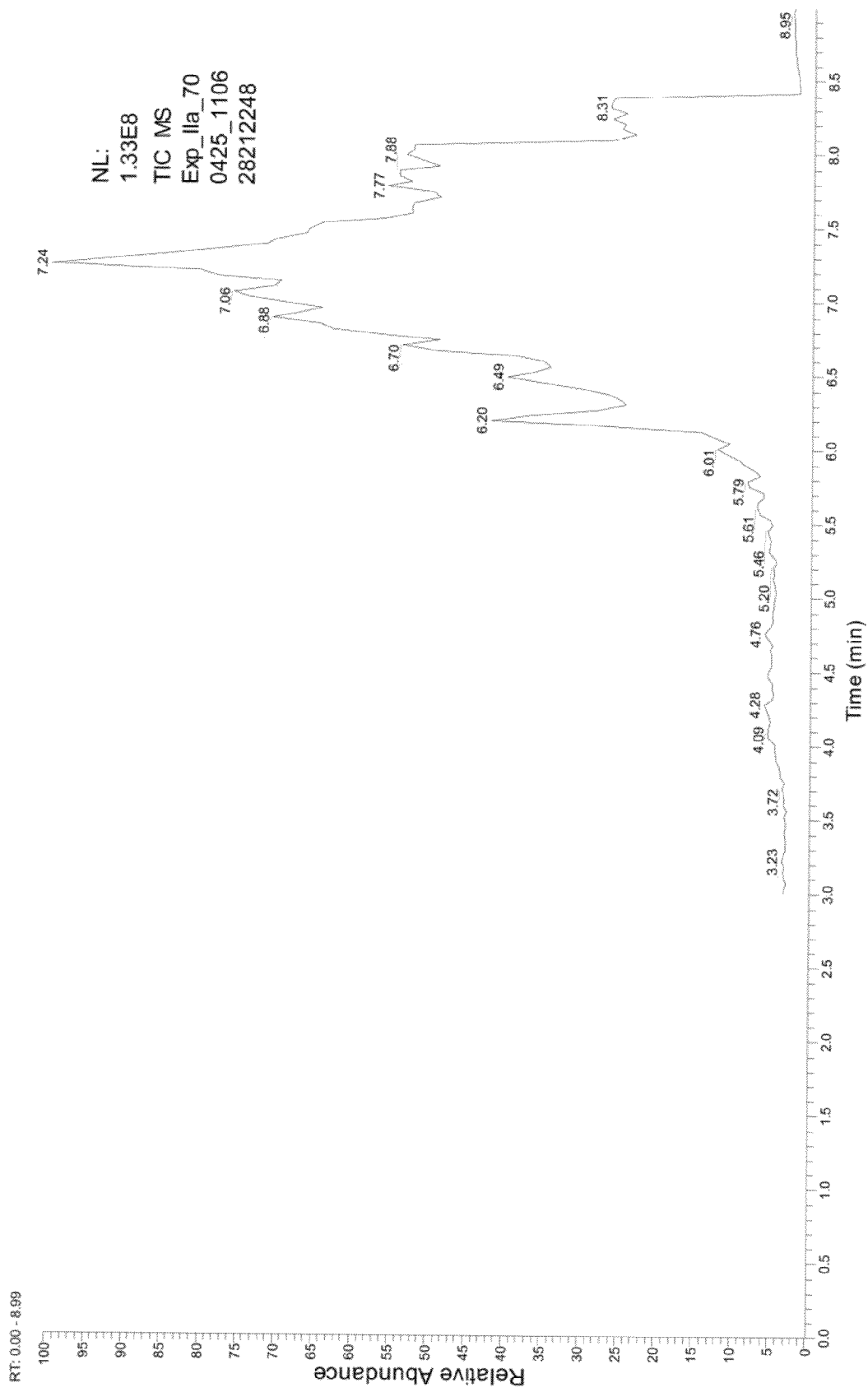
Figure 11C:
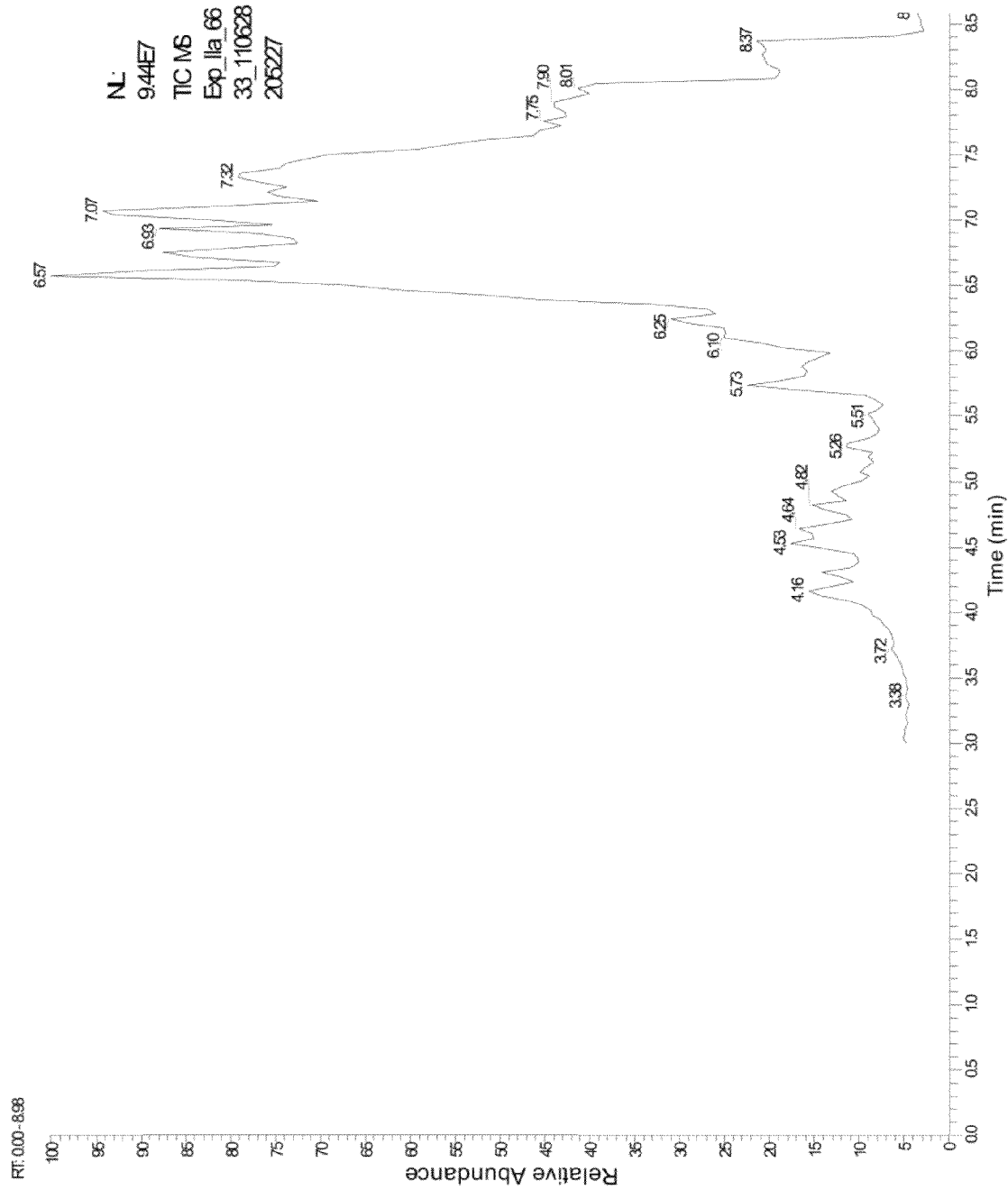

FIGS. 11A-11C illustrate FPCS-MS total ion current profiles of various microorganisms grown on the Oxoid Tryptic Soy Agar at 34 C for 20 h. (A)—*Escherichia coli* ATCC 8739; (B)—*Enterococcus gallinarum* ATCC 700425; (C)—*Bacillus subtilis* subs. *spizizenii* ATCC 6633. The total information about the analytes in a sample is compiled from the data which are extracted from each mass spectrum across the whole chromatographic run thus representing all co-eluting "sets" of analytes. As there are practically no chromatographic peaks (for example, 3-5 broad peaks across the whole 5 min gradient, as it is illustrated in FIGS. 11A-11C), all necessary information is derived from the mass spectra (m/z, intensity) with the only information that originate from the LC run, is the time of co-elution of the "sets" of analytes (only some of the original mixture components are represented in the mass spectrum due to the ionization/separation effects, as described above).

FPCS-MS requires no special columns, or small columns, or unusually shaped columns (for example, V-shaped columns) in combination to high flow rates, as is generally practiced for "ballistic chromatography" or "ballistic gradients". The columns used in FPCS-MS may be standard chromatographic columns. For example, the length of a column can be 20 mm, 30 mm, 50 mm, 100 mm, 150 mm, 250 mm and so on and/or the internal diameter of such a column can be 2.1 mm, 1 mm, 500 um, 150 um, 75 um and so on. Particle sizes and pore sizes are also standard as known in the art.

The flow rates that are used in FPCS-MS, are standard for the type of a column in use. For example, flow rate may be 900 µl/min, 400 µl/min, 100 µl/min, 30 µl/min, 200 nl/min, and so on.

By varying the chromatographic conditions (column dimensions and chemistry, particle and pore size, mobile phases and modifiers of the mobile phases), types of chromatography and off-line fractionation of complex samples with the individual fractions still remaining complex mixtures, one can focus on very different sets of components of the original complex mixtures.

Figure 12:
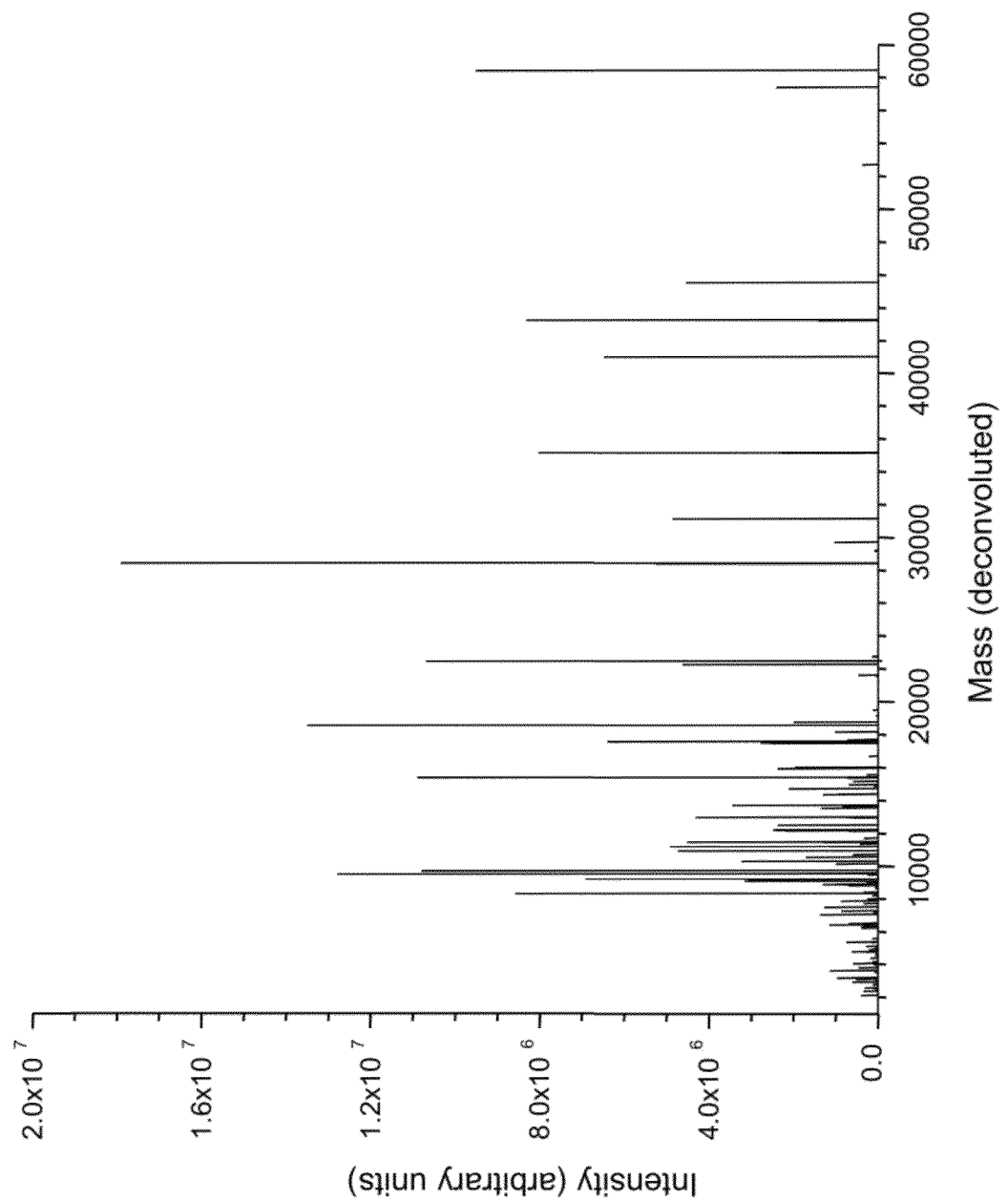
FIG. 12 illustrates deconvoluted masses of proteins derived from the information obtained in FPCS-MS of *Escherichia coli* ATCC 8739 grown on the Oxoid Tryptic Soy Agar at 34 C for 20 h shown in FIG. 11A

As mass spectrum for the co-eluting analytes may be recorded from as little as just one mass spectrometer scan, the information which can be obtained about the analytes in mixture, is very abundant, as illustrated in FIG. 12.

In combination, the extremely high resolution and mass accuracy that is delivered by the use of electrostatic ion trap which is the part of such mass spectrometers as Q-Exactive, Exactive mass spectrometers (Thermo Fisher Scientific) or similar mass spectrometers, provide a powerful tool for the discovery and targeted analysis of, for example, virulence factors, biomarkers for antibiotic resistance and/or susceptibility, differentiation of strains and so on.

Overall, FPCS-MS provides rapid analysis, maximizing the number of samples that can be analyzed in a set period of time, while providing the necessary information about the sample.

In a preferred embodiment, the mobile phase composition in a reversed-phase chromatographic separation is ramped in a much more rapid fashion for the chromatographic column used resulting in proteins of widely varying molecular weights eluting from the chromatographic column together.

The stationary phase in the chromatography column may be porous or non-porous silica or agarose particles, or a monolithic material polymerized or otherwise formed inside the column. The stationary phase may be coated with an appropriate material such as $C_{18}$, $C_8$, $C_4$ or another suitable derivative to facilitate the separation of the proteins, and such material may be chemically bonded to the particles or monolith inside the column. Particle sizes typically range from about 1.5 to 30 μm. Pore sizes can range from 50 to 300 angstroms. Inside diameters of columns typically range from about 50 μm to 2.1 mm, and column length from about 0.5 cm to 15 cm and above. The mobile phase or eluent may be a pure solvent, or a mixture of two or more solvents, and may contain added salts, acids and/or other chemical modifiers. The proteins are separated on the column or two sequentially or in parallel (as it is in the two dimensional chromatography) connected columns based on one or more physiochemical properties, including size, net charge, hydrophobicity, affinity, or other physiochemical properties. Chromatographic separation methods include one or more of ion exchange, size exclusion, hydrophobic interaction, affinity, normal-phase, reverse-phase or other chromatography.

In one embodiment, a reversed-phase chromatographic separation is performed on a 50-mm×2.1-mm internal diameter (ID) chromatographic column packed with 1.9 um particles and pore size 175 angstrom ($C_{18}$ stationary phase) using the following two mobile phases: 0.2% formic acid in water (mobile phase A) and 0.2% formic acid in acetonitrile (mobile phase B) at the flow rate 400 μl/min. Separation is performed in a 2-80% gradient of mobile phase B in mobile phase A within 2, 5 or 8 min.

In order to accommodate rapid analysis and sample turnaround time, the gradient is run on the order of approximately 8 minutes or less in one embodiment of the present invention. This compressed gradient format results in proteins with widely varying molecular weights eluting closely together. Using this embodiment, proteins up to 70 kDa mass can be detected. A significant advantage of this method is the improved specificity of detection obtained from higher mass ranges. The mass range of the ESI/MS-based method significantly exceeds that of MALDI methods, which have a practical upper limit of about 12-15 kDa mass, and, in addition, all of the proteins typically observed in a MALDI spectrum are found in the ESI/MS mass spectrum.

In the other embodiments, a chromatographic column with 0.32 mm ID or smaller and packed with a $C_4$ stationary phase is used with a 20-60% gradient of mobile phase B (acetonitrile with 0.2% formic acid) in mobile phase A (water with 0.2% formic acid) at a flow rate of approximately 10 μL/min. The gradient elution time for the chromatographic separation may range from approximately 10 minutes to 20 minutes, followed by a short re-equilibration time that is typically less than the separation time.

III. Ionization and Mass Spectrometry

Referring to step 120 of FIG. 1A, the sample may be ionized and subjected to mass spectrometric analysis as described in greater detail elsewhere herein. Referring to FIGS. 8A-8E, protein extracts from *B. Licheniformis, C. albicans, K. rosea, S. xylosus*, and *M. smegmatis* were partially separated by the FPCS-MS procedure described above. The separation was performed on a 5 cm×2.1 mm i.d. column packed with Hypersil Gold $C_{18}$-like column with 1.9μ particle size and a pore diameter of 170 angstroms. Solvent A was composed of 100% $H_2O$ and 0.2% formic acid and solvent B was made up of 100% ACN and 0.2% formic acid. Starting conditions were 98% A and 2% B at a flow rate of 400 μL/min and a column temperature of 40° C. Tandem mass spectrometry was performed using data dependent analysis of the top three most intense peaks associated with the full scan analysis. Masses that underwent MS/MS were placed on the dynamic exclusion list for a period of 20 seconds. The resulting tandem mass spectra were searched via version 3.0 of ProSight PTM software.

The data shown in FIGS. 8A-8E illustrate that the FPCS-MS works for a wide range of organisms across different microbial genera. In addition, one will appreciate that the FPCS-MS procedure described herein allows the second analysis procedure of steps 116-122 of FIG. 1A to be performed much more rapidly as compared to procedures where specific gradients and, in some cases, specific mobile phases are run for different organisms. Likewise, because the procedure described herein does not depend on baseline chromatographic separation of the components of the mixture, the gradient can be run much faster (e.g., 5 minutes vs. 30 minutes or vs. 90 minutes). It is actually a virtue of the method described that there is a lack of baseline separation and that the components crowd together when they come off the column. For example, as described above, the forced co-elution of subsets of proteins causes suppression of ionization of the mixture. Although ion suppression is generally considered to be disadvantageous, in this case ion suppression has the effect of simplifying the ion spectrum of the complex mixture coming off of the column by virtue of the fact that a signal results from only the most ionizable and plentiful proteins in the recorded in the mass spectrum.

IV. Strain Typing

As shown in step 122 of FIG. 1A, protein(s) specific to a given strain or serovar type may be used for typing individual isolates. Variation within microorganism isolates is often the result of deletion and/or insertion of entire gene(s). Therefore, it follows that different strains may potentially lack or gain hundreds of strain-specific proteins and this variation may provide a uniquely discriminatory typing system.

In one example, twelve strains of *E. coli* were analyzed using the methods of the present invention. The ability of the present invention to detect a bigger number of proteins, proteins of higher molecular weights and with better mass accuracy than those detected using conventional MALDI methods was tested in connection with variations of a 35.4 kDa protein found in each of the twelve strains. As shown in Table 1, five different forms of a protein having a mass of approx. 35 KDa were detected.

TABLE 1

| Mass of the common protein (Da) | ATCC Strain of E. coli | | | | | | | | | | | |
|---|---|---|---|---|---|---|---|---|---|---|---|---|
| | 11775 | 35218 | 4157 | 14948 | 8739 | 33876 | 43888 | 51446 | 10536 | 11229 | 35421 | 29194 |
| 35,167 | ✓ | ✓ | — | — | — | — | — | — | — | — | — | — |
| 35,176 | — | — | ✓ | ✓ | ✓ | ✓ | ✓ | ✓ | — | — | — | — |
| 35,413 | — | — | — | — | — | — | — | — | ✓ | — | — | — |
| 35,426 | — | — | — | — | — | — | — | — | — | ✓ | — | — |
| 35,497 | — | — | — | — | — | — | — | — | — | — | ✓ | ✓ |

One can see from the Table 1, that the strains of E. coli can be grouped according to the common protein which yet has a different mass due to the variations in the amino acid sequence. This protein has MW 35413 Da in ATCC 10536 and MW of 35426 Da in ATCC 11229 MW of 35497 Da was observed for this protein in two strains (ATCC 35421 and ATCC 29194). Likewise, this protein has MW of 35167 Da when isolated from two other strains, namely ATCC 11775 and ATCC 35218 and MW of 35176 Da was found in five different strains. The protein was detected at the same retention time in twelve ATCC strains of E. coli to illustrate the utility of the present invention for distinguishing between closely related strains of microorganisms according to one embodiment of the invention. The mass spectra contain also other proteins that vary in different strains (either the same proteins which amino acid sequence vary, or different proteins in different strains). Detection of multiple proteins as the part of identification procedure and use of tandem mass spectrometry provides accurate results and the confidence when typing the strains.

V. Characterization of Virulence Factors and Resistance Mechanisms

A second analysis may also be used to identify virulence factors or antibiotic resistance and/or susceptibility markers present in the identified microorganisms. Such analysis may or may not require pre-treatment of the sample, for example, a brief exposure to one or more antibiotics or other stressful conditions (e.g., temperature, scarcity of one or more nutrients, iron deficiency, copper exposure, etc.) to induce proteins associated with resistance, susceptibility or virulence. For analysis of virulence factors and/or resistance markers, the mass spectrometer is run in the target MS/MS mode (product ion scanning) to detect known virulence factors or resistance markers.

Figure 9A:
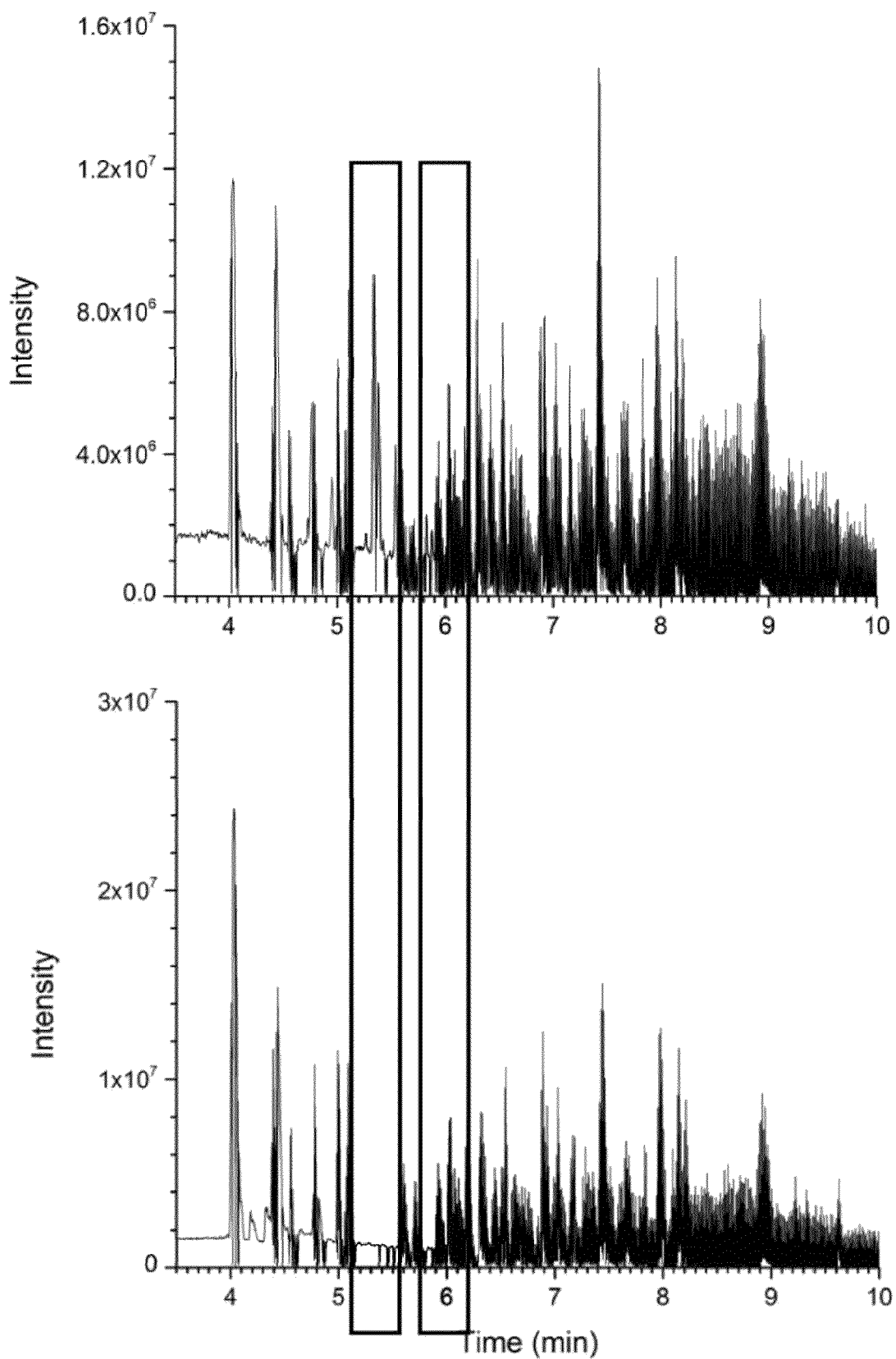
FIG. 9A shows MS data illustrating a comparison of an antibiotic resistant *E. coli* (ATCC 35218) grown under standard growth conditions and in the presence of oxacillin for an 18 hr period.
Figure 9B:
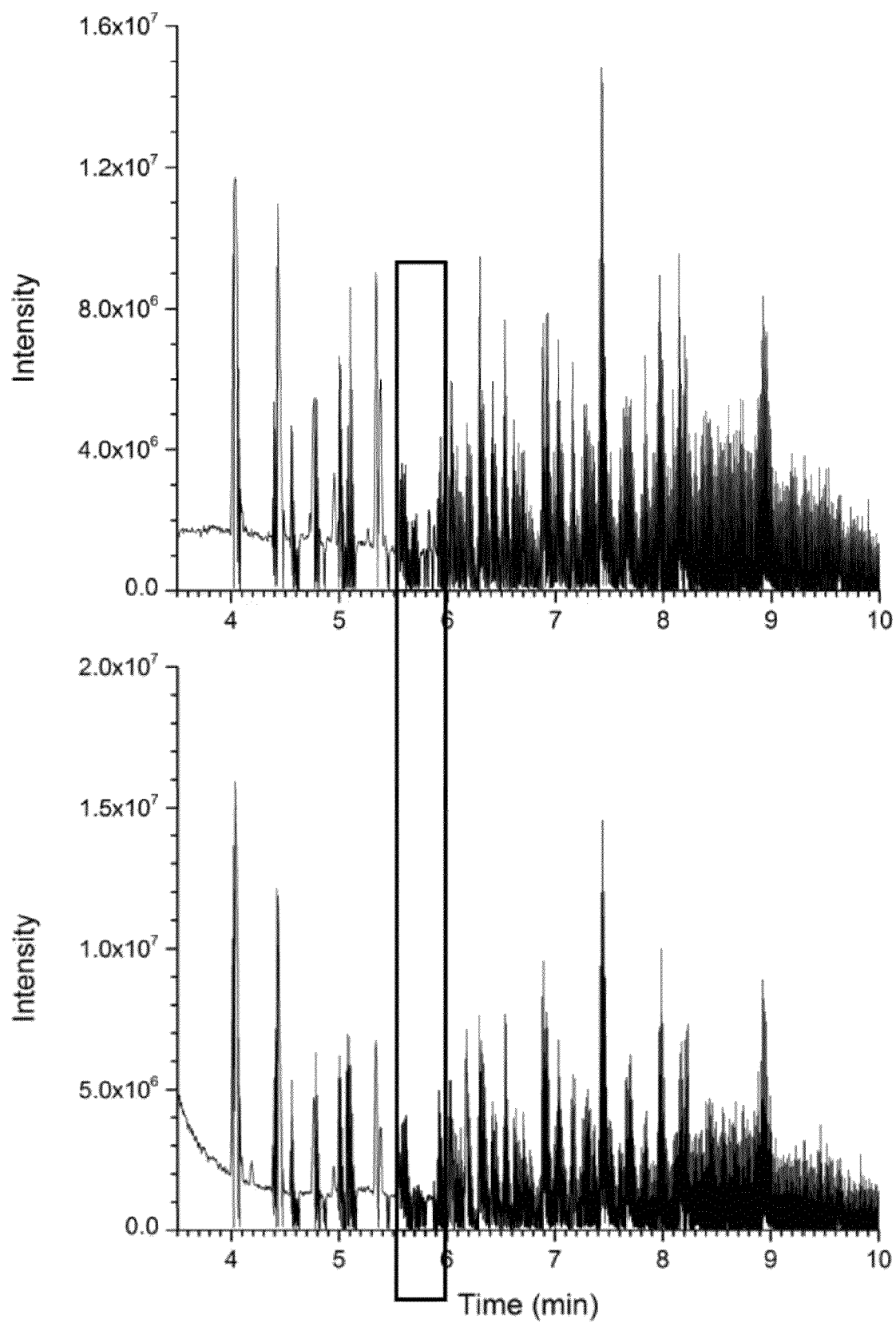
FIG. 9B shows MS data illustrating a comparison of the antibiotic resistant *E. coli* of FIG. 9A grown under standard growth conditions and in the presence of nafcillin for an 18 hr period.
Figure 9C:
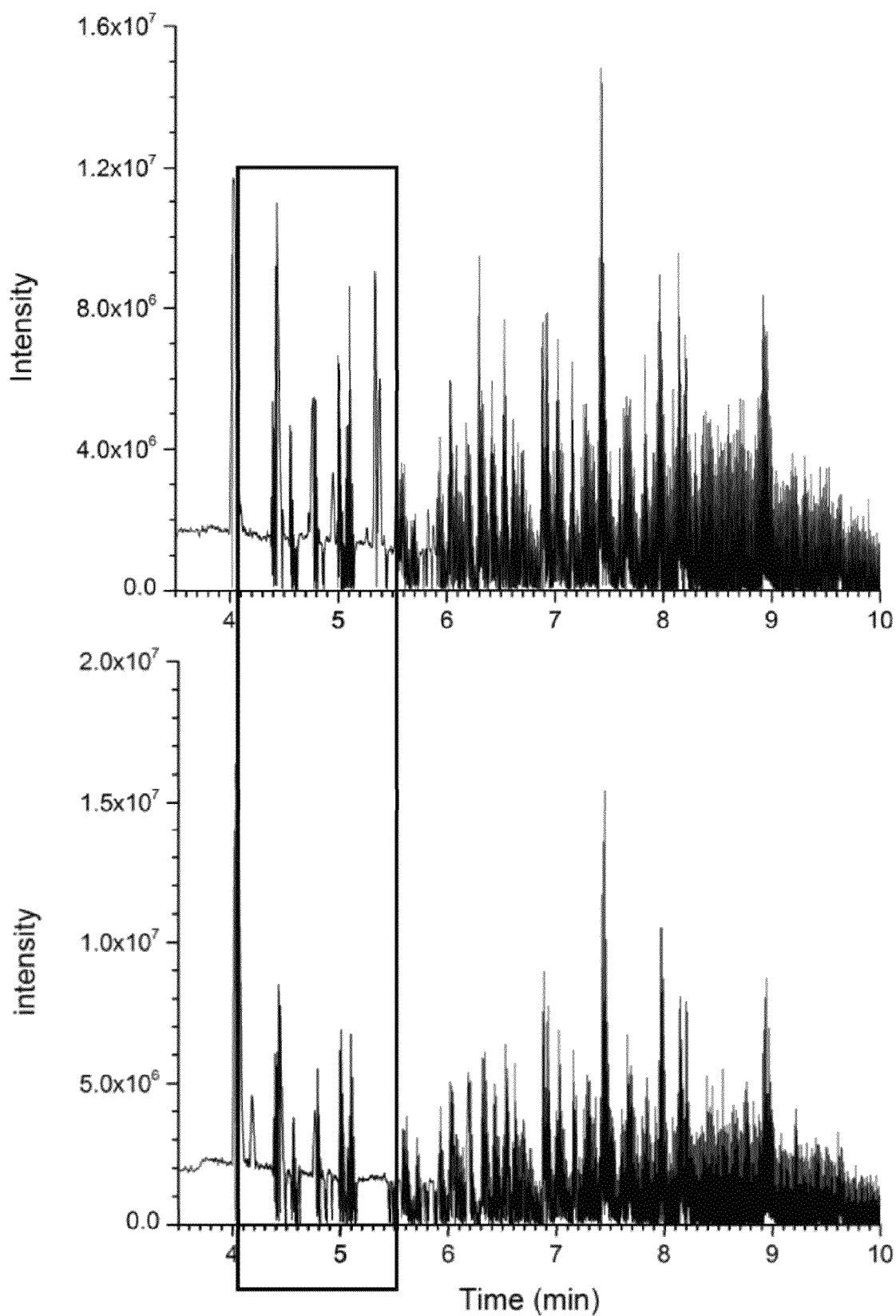
FIG. 9C shows MS data illustrating a comparison of the antibiotic resistant *E. coli* of FIG. 9A grown under standard growth conditions and in the presence of penicillin for an 18 hr period.
Figure 9D:
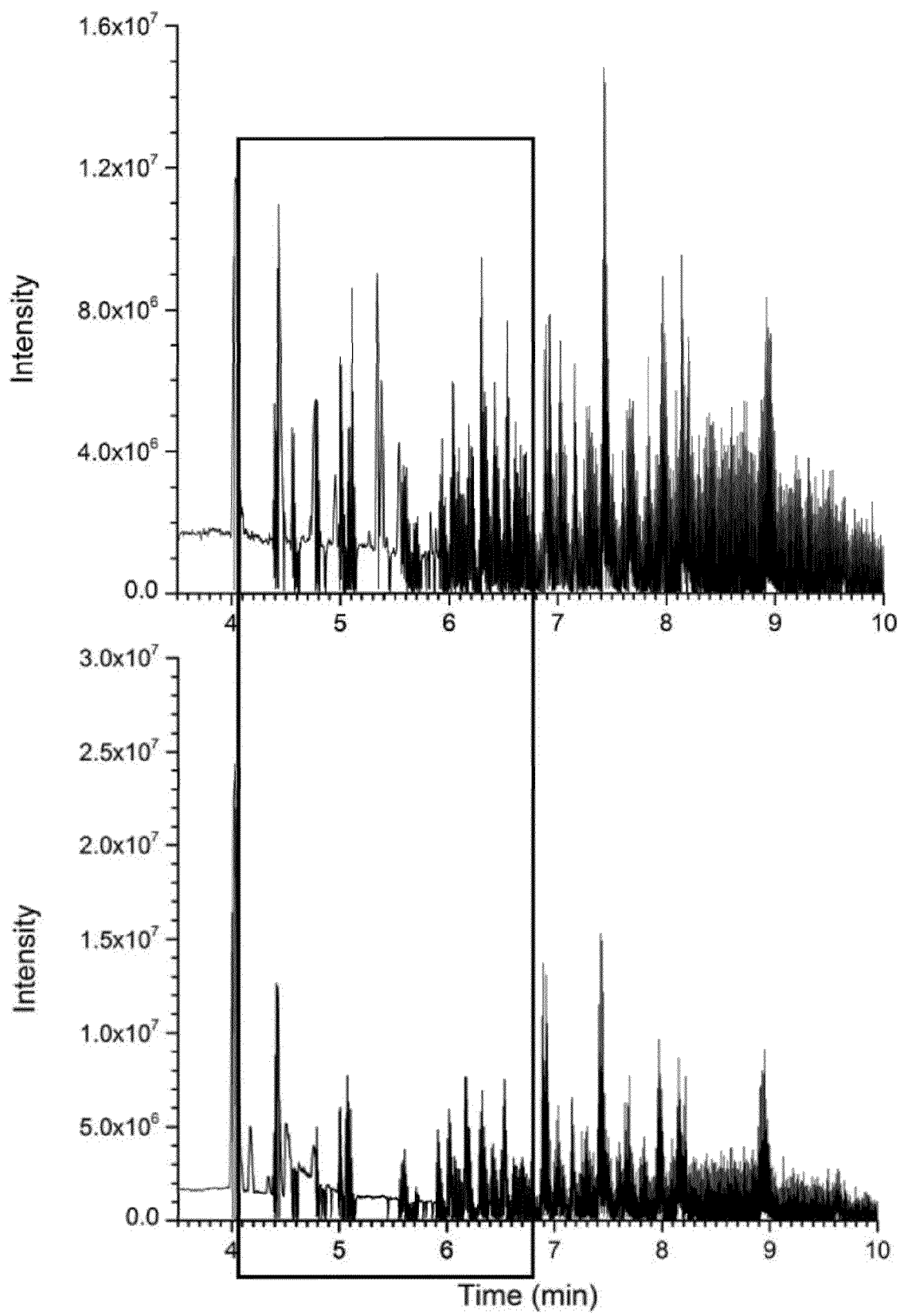
FIG. 9D shows MS data illustrating a comparison of the antibiotic resistant *E. coli* of FIG. 9A grown under standard growth conditions and in the presence of ampicillin for an 18 hr period.

This principle is illustrated in FIGS. 9A-9D. In FIGS. 9A-9D, an antibiotic resistant strain of E. coli (ATCC 35218) was grown in the presence and absence of antibiotics at 37° C. for 18 hours on the Oxoid Mueller-Hinton Agar (Thermo Fisher Scientific). In FIG. 9A, cells were grown in the presence of oxacillin; in FIG. 9B, cells were grown in the presence of naficillin; in FIG. 9C, cells were grown in the presence of penicillin; and in FIG. 9D, cells were grown in the presence of ampicillin. In each of the examples, the boxed regions indicate portions of the chromatograms where significant changes are observed in mass spectra obtained for the cells that originate from antibiotic treated and not treated cultures. In the mass spec experiment, changes in protein expression are shown. However, changes resulting from antibiotic exposure may include alterations in protein expression, lipids, and small molecules either individually or combined to indicate antibiotic resistance.

It is possible to detect certain resistance, sensitivity or virulence markers after a brief incubation with antibiotic of approximately 10 minutes or less. Further, analysis of resistance markers and/or virulence factors may be quantitative. The marker information is useful for patho-typing and characterization of a microorganism for purposes of patient treatment or for collecting epidemiologic information.

In one embodiment of the invention, top-down proteomics may be used to investigate the various forms of the resistance marker, β-lactamase. Multiple β-lactamase types (AmpC, ESBL, KPC, etc.) can occur in the same cell leading to errors in screening and confirmatory phenotypic tests. Resistance marker information may be used to verify and correct conventional phenotypic susceptibility results. For example, changes in porins and/or AmpC over expression can mimic the phenotype of ESBL. The presence of a KPC beta lactamase masks the phenotype of an ESBL. These proteins can be identified using the top-down method of the present invention since MS/MS methods are capable of detecting any change or substitution in the amino acid sequence of the intact protein.

A direct comparison to a traditional bottom-up procedure commonly used by proteomics laboratories further emphasizes the advantages of the top-down method of the present invention. By way of example, if the entire DNA sequence of the organism is known before analysis is performed, one can judge whether the β-lactamase enzyme might be expressed. If the β-lactamase is indeed expressed, then there is a chance that one or more peptides associated with the enzyme can be identified in a bottom-up proteomics experiment. If the peptide(s) identified is/are specific to that one β-lactamase in 1000 known variants of β-lactamase, then one can say unequivocally that a specific type is confirmed. However, the detected and identified peptide may happen to be common to many different variants of β-lactamase. Even distinguishing two E. coli strains wherein β-lactamase variants differ by a few as two amino acids is limited, if not impossible, using a bottom-up approach.

In another embodiment of the invention, unique forms of resistance markers, such as β-lactamases, may be used to facilitate identification of a given microorganism. For example, a direct comparison of specified extended spectrum beta-lactamases (ESBL) across all known microorganisms reveals only two species with 100% homology, namely Pseudomonas aeruginosa and Acinetobacter baumannii. If the particular ESBL is expressed and detected, then microbial identification is narrowed to two organisms without even considering any other proteins. The identification of one or more proteins may be sufficient to confirm identification of each.

As a further example, a search of a common variant β-lactamase specific to E. coli against all known sequences for similarity may be performed. However, a slight modification of the enzyme yields a variant common to many different microorganisms. The β-lactamase specific to *E. coli* may be used to differentiate *E. coli* from *Shigella*. It is of note that the (β-lactamase of *Shigella flexneri* and *Shigella dysenteriae* contain a β-lactamase comprising 286 amino acids which is the number found in *E. coli* β-lactamase; however the sequence of the *Shigella* version of β-lactamase differs by one amino acid (substitution of a glycine for serine) which is sufficient to provide for accurate identification of the microorganisms.

For samples comprising a mixture of microorganisms, the diagnostic information provided by a resistance marker sequence may be used to determine the microorganism expressing each antibiotic resistance marker. Other resistance markers capable of providing useful information include, without limitation, DNA gyrases, aminoglycisidases, efflux pumps (SrpA and MFP), proteins involved in folate metabolism, and rRNA binding proteins.

In another embodiment of the invention, specific marker panels of target proteins may be used to determine the identity of a microorganism. These panels may require monitoring the intensity profiles of specific proteins as a function of time. A hybrid tandem mass spectrometer that employs a single stage quadrupole followed by a series of ion transfer devices, a low energy collision cell, a C-trap, an HCD cell and orbitrap mass analyzer is used to identify target proteins. Protein identification is accomplished via MS/MS analysis of intact proteins and searched against a reduced microbial proteome database containing only proteins of relevance to the specific microorganism or group of microorganisms.

Figure 10:
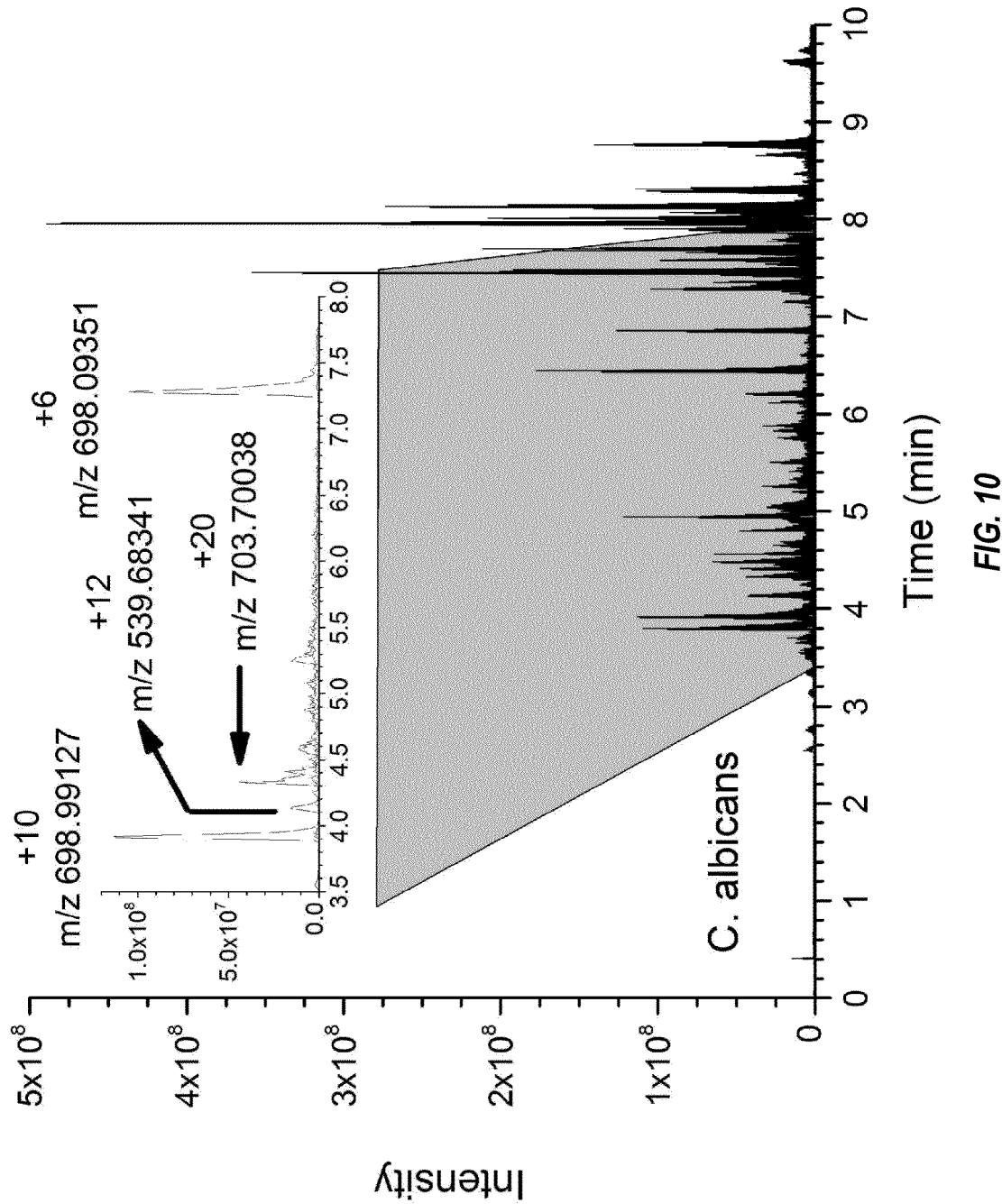
FIG. 10 illustrates high resolution/mass accuracy extracted ion profiles from four different proteins derived from *C. albicans*.

This principle is demonstrated in FIG. 10. Part of characterizing an identified pathogen is to examine the potential of resistance markers, virulence factors, strain typing, and antibiotic susceptibility on patient outcomes. In addition to identifying targets via full scan or selected ion monitoring, quantitation may be required in some instances to determine if the levels of a virulence factor (for example adhesions, phospholipases, and secreted aspartyl proteases) are critical enough to affect patient outcomes. Here in FIG. 10, high resolution/mass accuracy data of extracted ion profiles from four different proteins derived from *C. albicans* is illustrated. These ions at m/z values of 539.68341 (+12), 698.09351 (+6), 698.99127 (+10), and 703.70038 (+20) correspond to proteins with masses of 6.46, 7.27, 6.97, and 14.0 kDa spread across a retention time range between 3.5 and 8.0 minutes as shown in the inset. Quantitation can be accomplished using external or internal standard methods, standards addition, or relative quantitative approaches. Examples include the use of label free techniques, selected reaction monitoring, in-line spectroscopic approaches, metabolic labeling, or chemical labeling. Peak areas or heights can be used for amount calculations along with values obtained for each charge state of a given protein by using resolved or unresolved isotopic clusters.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for identifying one or more unknown microbes, comprising:
   a) providing a sample containing one or more unknown microbes;
   b) disrupting the one or more unknown microbes present in the sample to provide a fluid extract;
   c) separating a soluble protein fraction from an insoluble protein fraction present in the fluid extract and preparing a solution containing soluble, intact proteins from the one or more unknown microbes;
   d) injecting the solution into an ion source of a mass spectrometer system and ionizing a stream or flow of the solution to form ionized proteins;
   e) analyzing the ionized proteins with a mass analyzer of the mass spectrometer system, wherein analyzing comprises:
      i) in a first mass spectrometry step, acquiring one or more mass spectra representative of one or more of the soluble proteins in the sample;
      ii) determining molecular weights for the proteins from the one or more mass spectra;
      iii) using the determined molecular weights to search a first database containing molecular weights of known microbial proteins to identify, for a second mass spectrometry step, a set of intact target proteins representative of a subset of candidate microbes;
      iv) in the second mass spectrometry step, selecting one or more precursor ions from the set of intact target proteins and fragmenting the precursor ions in the mass spectrometer by fragmentation means to produce a plurality of product ions;
      v) using mass-to-charge ratios of the plurality of product ions to search a second database containing molecular weights of known microbial proteins and at least one of product ion m/z values, amino acid sequence, or post-translational modification information of said known microbial proteins, wherein the subset of candidate microbes from the first database is used to limit a search of the second database; and
   f) using information obtained in step (e) for one or more proteins from each of the one or more unknown microbes in the sample to identify at least one of the unknown microbes, wherein steps (b)-(f) are completed in less than 25 minutes.

2. The method of claim 1, wherein step (b) is effective for Gram-positive bacteria, Gram-negative bacteria, yeast, viruses, mycobacteria and filamentous fungi.

3. The method of claim 1 or claim 2, wherein the solution of soluble proteins is streamed directly into an ionization apparatus.

4. The method of claim 1, wherein the ionization is electrospray ionization.

5. The method of claim 1, wherein in the first mass spectrometry step the mass spectra for the one or more of the proteins in the sample have a mass accuracy of at least 15 parts-per-million.

6. The method of claim 1, wherein the fragmentation means is collision-induced dissociation.

7. The method of claim 1, wherein in the second mass spectrometry step the mass-to-charge ratios for the product ions have a mass accuracy of at least 15 parts-per-million or better.

8. The method of claim 1, wherein steps (b)-(f) are performed using automated instrumentation.

9. The method of claim 1, wherein step (c) is performed using a solid-phase extraction device comprising bonded silica sorbents, polymeric sorbents, or chelating agents.

10. The method of claim 1, wherein prior to step (b), the sample is pre-treated with a solvent that facilitates disruption of the one or more microbes.

11. The method of claim 1, wherein prior to step (b) the sample is pre-treated with one or more organic solvents, provided that if only one organic solvent is used, the one organic solvent is other than ethanol.

12. A method for identifying one or more unknown microbes, comprising:
   a) providing a sample suspected of containing one or more unknown microbes;
   b) disrupting the one or more unknown microbes present in the sample to provide a fluid extract;
   c) separating a soluble protein fraction from an insoluble protein fraction present in the fluid extract and preparing a solution containing intact, soluble proteins from the one or more unknown microbes;
   d) injecting the solution into an ion source of a mass spectrometer system and ionizing a stream or flow of the solution to form ionized proteins;
   e) analyzing the ionized proteins with a mass analyzer of the mass spectrometer system, wherein analyzing comprises:
      i) in a first mass spectrometry step, acquiring one or more mass spectra representative of soluble proteins in the sample;
      ii) determining molecular weights for the soluble proteins from the one or more mass spectra;
      iii) using the determined molecular weights to search a first database containing molecular weights of known microbial proteins to identify, for a second mass spectrometry step, a set of target proteins representative of a subset of candidate microbes;
      iv) in a second mass spectrometry step, selecting one or more precursor ions of the proteins from the one or more ionized proteins of the sample and fragmenting the precursor ions in the mass spectrometer by fragmentation means to produce a plurality of product ions;
      v) using mass-to-charge ratios of the plurality of product ions to search a second database containing molecular weights of known microbial proteins and at least one of amino acid sequence or post-translational modification information of said known microbial proteins, wherein the subset of candidate microbes from the first database is used to limit a search of the second database; and
   f) automatically analyzing a sufficient number of proteins to identify at least one of the one or more unknown microbes in said sample, wherein steps (b)-(f) are completed in less than 25 minutes.

13. The method of claim 12, wherein at least one of the first or the second mass spectrometry step comprises selecting said one or more precursor ions from a mass range window, and repeating said second mass spectrometry step until a sufficient number of mass range windows have been covered to identify at least one of the one or more microbes in said sample.

14. The method of claim 12, wherein step (c) is performed using a solid-phase extraction device comprising bonded silica sorbents, polymeric sorbents, or chelating agents.

15. The method of claim 12, wherein prior to step (b), the sample is pre-treated with a solvent that facilitates disruption of the one or more microbes.

16. The method of claim 12, wherein prior to step (b) the sample is pre-treated with one or more organic solvents, provided that if only one organic solvent is used, the one organic solvent is other than ethanol.

17. A method for identifying and characterizing one or more unknown microbes, comprising:
   a) providing a first aliquot of a sample containing one or more unknown microbes;
   b) disrupting the one or more unknown microbes present in the first aliquot to provide a fluid extract;
   c) separating a first soluble protein fraction from an insoluble protein fraction present in the fluid extract and preparing a first solution of soluble proteins;
   d) injecting the first solution into an ion source of a mass spectrometer system and ionizing the first solution to form ionized proteins;
   e) analyzing the ionized proteins with a mass analyzer of the mass spectrometer system, wherein analyzing comprises:
      i) in a first mass spectrometry step, acquiring one or more first mass spectra representative of soluble proteins in the sample;
      ii) determining molecular weights for the soluble proteins based upon the one or more first mass spectra;
      iii) using the determined molecular weights to perform a first search of a first database containing molecular weights of known microbial proteins to identify, for a second mass spectrometry step, a set of target proteins representative of a first subset of candidate microbes;
      iv) in the second mass spectrometry step, selecting one or more first precursor ions of the one or more first ionized proteins and fragmenting in the mass spectrometer the first precursor ions by fragmentation means to produce a first plurality of first product ions;
      v) using mass-to-charge ratios of the first plurality of first product ions to perform a first search of a second database containing molecular weights of known microbial proteins and at least one of product ion m/z values, amino acid sequence or post-translational modification information of said known microbial proteins, wherein the first subset of candidate from the first database is used to limit the first search of the second database;
   f) using information obtained in step (e) for one or more soluble proteins from each of the one or more unknown microbes in the sample to identify at least one of the microbes to the genus species level, wherein steps (b)-(f) are completed in less than 25 minutes;
   g) using information from step (f) to automatically select a second analytical method from a list of pre-defined analytical methods, the second method also using mass spectrometry;
   h) providing a second aliquot of the fluid extract or of a second fluid extract of the same sample;
   i) separating a second soluble protein fraction from an insoluble protein fraction present in the second aliquot and preparing a second solution of soluble proteins;
   j) subjecting the second solution to a separation to provide a subset of soluble proteins;
   k) injecting the second solution into an ion source of a mass spectrometer system and ionizing a stream or flow of the subset of soluble proteins to form one or more second ionized proteins;
   l) analyzing the one or more second ionized proteins with the mass analyzer of the mass spectrometer system, wherein analyzing comprises:
      i) in a third mass spectrometry step, acquiring one or more second mass spectra representative of one or more soluble proteins in the subset of soluble proteins;
      ii) determining molecular weights for the one or more soluble proteins in the subset of soluble proteins from the one or more second mass spectra;

iii) performing a second search of the first database and selecting a second subset of the candidate microbes from the database on the basis of the determined molecular weights of the one or more soluble proteins in the subset of soluble proteins;

iv) in a fourth mass spectrometry step, selecting one or more second precursor ions of the one or more second ionized proteins and fragmenting in the mass spectrometer the second precursor ions by fragmentation means to produce a second plurality of product ions;

v) using mass-to-charge ratios of the second plurality of product ions to perform a second search of the second database, wherein the second subset of tentatively identified microbes from the first database is used to limit the second search of the second database;

m) using information obtained in step (l) to identify and, optionally to quantitate, one or more soluble proteins indicative of any of: strain and/or serovar identification, antibiotic resistance, antibiotic susceptibility, virulence or any combination thereof, wherein the method includes no chemical or enzymatic digestion of the proteins in the first or second aliquot of the sample.

18. The method of claim 17, wherein the second analytical method is performed using a second fluid extract of the same sample.

19. The method of claim 17, wherein step (c) is performed using a solid-phase extraction device comprising bonded silica sorbents, polymeric sorbents, or chelating agents.

20. The method of claim 11, wherein the separation of step (j) comprises rapid, time-compressed chromatography which provides partial separation of proteins in the second solution of the second soluble protein fraction.

21. The method of claim 17, wherein prior to step (b), the sample is pre-treated with a solvent that facilitates disruption of the one or more microbes.

22. The method of claim 17, wherein prior to step (b) the sample is pre-treated with one or more organic solvents, provided that if only one organic solvent is used, the one organic solvent is other than ethanol.

23. The method of claim 17, wherein steps (a)-(m) are performed using automated instrumentation.

* * * * *